US011312966B2

(12) United States Patent
Marui et al.

(10) Patent No.: US 11,312,966 B2
(45) Date of Patent: Apr. 26, 2022

(54) NUCLEIC ACID FOR TREATING MITE ALLERGY

(71) Applicant: Astellas Pharma Inc., Tokyo (JP)

(72) Inventors: Takanori Marui, Tokyo (JP); Masao Uchida, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 17/377,297

(22) Filed: Jul. 15, 2021

(65) Prior Publication Data

US 2021/0340549 A1 Nov. 4, 2021

Related U.S. Application Data

(63) Continuation of application No. 17/054,340, filed as application No. PCT/JP2019/018657 on May 10, 2019.

(30) Foreign Application Priority Data

May 11, 2018 (JP) ................................ 2018-091963

(51) Int. Cl.

| | |
|---|---|
| ***C07K 14/435*** | (2006.01) |
| ***C07K 14/705*** | (2006.01) |
| ***C07K 19/00*** | (2006.01) |
| ***A61K 39/35*** | (2006.01) |
| ***A61K 38/17*** | (2006.01) |
| ***C12N 15/62*** | (2006.01) |
| ***C12N 15/63*** | (2006.01) |
| ***A61P 37/08*** | (2006.01) |
| ***C12N 9/50*** | (2006.01) |
| *A61K 39/00* | (2006.01) |

(52) U.S. Cl.

CPC ............ *C12N 15/62* (2013.01); *A61K 38/177* (2013.01); *A61K 39/35* (2013.01); *A61P 37/08* (2018.01); *C07K 14/43531* (2013.01); *C07K 14/70596* (2013.01); *C07K 19/00* (2013.01); *C12N 9/50* (2013.01); *C12N 15/63* (2013.01); *C12Y 304/22065* (2013.01); *A61K 2039/5256* (2013.01); *A61K 2039/53* (2013.01); *A61K 2039/57* (2013.01); *C07K 2319/02* (2013.01); *C07K 2319/03* (2013.01); *C07K 2319/06* (2013.01)

(58) Field of Classification Search

CPC ....... A61P 37/08; A61K 39/35; A61K 38/177; C07K 2319/02; C07K 2319/03; C07K 14/43531; C07K 14/70596; C07K 2319/06; C07K 14/705; C07K 19/00; C12N 15/62

See application file for complete search history.

(56) References Cited

U.S. PATENT DOCUMENTS

| | | | |
|---|---|---|---|
| 5,972,352 | A | 10/1999 | Thomas et al. |
| 2006/0251667 | A1 | 11/2006 | Chua et al. |
| 2009/0104208 | A1 | 4/2009 | Valenta et al. |
| 2016/0185831 | A1 | 6/2016 | Hearl et al. |
| 2017/0136121 | A1 | 5/2017 | Thalhamer et al. |
| 2017/0304432 | A1 | 10/2017 | Hearl et al. |
| 2019/0351050 | A1 | 11/2019 | Heiland |

FOREIGN PATENT DOCUMENTS

| | | | |
|---|---|---|---|
| WO | WO-88/10297 | A1 | 12/1988 |
| WO | WO-2004/019978 | A1 | 3/2004 |
| WO | WO-2007/124524 | A1 | 11/2007 |
| WO | WO-2009/040443 | A1 | 4/2009 |
| WO | WO-2013/187906 | A1 | 12/2013 |
| WO | WO-2015/200357 | A2 | 12/2015 |
| WO | WO-2018/093932 | A2 | 5/2018 |

OTHER PUBLICATIONS

Bhattacharya et al. Impact of genetic variation on three dimensional structure and function of proteins. PLoS ONE 12(3): e0171355, 2017.*

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Dantzer et al. Next-generation approaches for the treatment of food allergy. Curr Allergy Asthma Report 19: 5, 2019 (8 total pages).*

Doerks et al. Protein annotation: detective work for function prediction. Trends in Genetics 14:248-250, 1998.*

Fenton et al. Rheostat positions: a new classification of protein positions relevant to pharmacogenomics. Medicinal Chem Res 29: 1133-1146, 2020.*

Guo et al. Protein tolerance to random amino acid change. Proc Natl Acad Sci USA 101(25): 9205-9210, 2004.*

(Continued)

*Primary Examiner* — Bridget E Bunner

(74) *Attorney, Agent, or Firm* — Foley & Lardner LLP

(57) ABSTRACT

[Problem] To provide a nucleic acid expected to be useful for treating mite allergy.

[Means to be solved] Provided is a nucleic acid comprising a nucleotide sequence encoding a chimeric protein, wherein the nucleic acid comprises a nucleotide sequence encoding a signal peptide, a nucleotide sequence encoding an intra-organelle stabilizing domain of LAMP, a nucleotide sequence encoding an allergen domain comprising Der p 1, Der p 2, Der p 23, and Der p 7, a nucleotide sequence encoding a transmembrane domain and a nucleotide sequence encoding an endosomal/lysosomal targeting domain of LAMP in this order.

12 Claims, 2 Drawing Sheets

Specification includes a Sequence Listing.

(56) References Cited

OTHER PUBLICATIONS

Ngo et al. "Computational complexity, protein structure prediction, and the Levinthal paradox" in The Protein Folding Problem and Tertiary Structure Prediction, pp. 492-495, 1994.*

Skolnick et al. From genes to protein structure and function: novel applications of computational approaches in the genomic era. Trends Biotechnol 18(I):34-39 2000.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Wells, J.A. Additivity of mutational effects in proteins. Biochemistry 29(37): 8509-8517, 1990.*

Banerjee et al,. "Der p 11 Is a Major Allergen for House Dust Mite-Allergic Patients Suffering from Atopic Dermatitis," J. Invest. Dermatol., Jan. 2015, 135(1):102-109.

International Search Report (with English translation) and Written Opinion dated Jul. 23, 2019 in PCT/JP2019/018657.

Mueller et al., "Serological, genomic, and structural analyses of the major mite allergen Der p 23," Clin. Exp. Allergy, Feb. 2016, 46(2):365-376.

Shen et al., "Characterization of the house dust mite allergen Der p 7 by monoclonal antibodies," Clinical and Experimental Allergy, 1995, 25:416-422.

Su et al., "CryJ-LAMP DNA Vaccines for Japanese Red Cedar Allergy Induce Robust Th1-Type Immune Responses in Murine Model," Journal of Immunology Research, 2016, Article ID 4857869, 15 pages.

Tan et al., "Intramuscular immunization with DNA construct containing Der p 2 and signal peptide sequences primed strong IgE production," Vaccine, 2006, 24:5762-5771.

Examination Report dated Nov. 1, 2020 and Official Notification dated Dec. 16, 2020 in corresponding GCC Patent Application No. GC 2019-37546.

Jongejan et al., "Modified Allergens and their Potential to Treat Allergic Disease," Curr. Allergy Asthma Rep., 2014, 14(12):478, 1-10.

Kim et al., "Protective effect of the DNA vaccine encoding the major house dust mite allergens on allergic inflammation in the murine model of house dust mite allergy," Clinical and Molecular Allergy, Feb. 20, 2006, 4:4, 1-9.

Supplementary European Search Report dated Dec. 17, 2021 in EP 19799639.0.

* cited by examiner

SEQUENCE LISTING

```
<160> NUMBER OF SEQ ID NOS: 3

<210> SEQ ID NO 1
<211> LENGTH: 3123
<212> TYPE: DNA
<213> ORGANISM: Artificial Sequence
<220> FEATURE:
<223> OTHER INFORMATION: Nucleic acid encoding a chimeric protein
<220> FEATURE:
<221> NAME/KEY: CDS
<222> LOCATION: (1)..(3123)

<400> SEQUENCE: 1

atg gcg ccc cgc agc gcc cgg cga ccc ctg ctg ctg cta ctg ctg ttg       48
Met Ala Pro Arg Ser Ala Arg Arg Pro Leu Leu Leu Leu Leu Leu Leu
1               5                   10                  15

ctg ctg ctc ggc ctc atg cat tgt gcg tca gca gca atg ttt atg gtg       96
Leu Leu Leu Gly Leu Met His Cys Ala Ser Ala Ala Met Phe Met Val
            20                  25                  30

aaa aat ggc aac ggg acc gcg tgc ata atg gcc aac ttc tct gct gcc      144
Lys Asn Gly Asn Gly Thr Ala Cys Ile Met Ala Asn Phe Ser Ala Ala
        35                  40                  45
```

-continued

```
ttc tca gtg aac tac gac acc aag agt ggc cct aag aac atg acc ctt      192
Phe Ser Val Asn Tyr Asp Thr Lys Ser Gly Pro Lys Asn Met Thr Leu
    50                  55                  60

gac ctg cca tca gat gcc aca gtg gtg ctc aac cgc agc tcc tgt gga      240
Asp Leu Pro Ser Asp Ala Thr Val Val Leu Asn Arg Ser Ser Cys Gly
65                  70                  75                  80

aaa gag aac act tct gac ccc agt ctc gtg att gct ttt gga aga gga      288
Lys Glu Asn Thr Ser Asp Pro Ser Leu Val Ile Ala Phe Gly Arg Gly
                85                  90                  95

cat aca ctc act ctc aat ttc acg aga aat gca aca cgt tac agc gtc      336
His Thr Leu Thr Leu Asn Phe Thr Arg Asn Ala Thr Arg Tyr Ser Val
            100                 105                 110

cag ctc atg agt ttt gtt tat aac ttg tca gac aca cac ctt ttc ccc      384
Gln Leu Met Ser Phe Val Tyr Asn Leu Ser Asp Thr His Leu Phe Pro
        115                 120                 125

aat gcg agc tcc aaa gaa atc aag act gtg gaa tct ata act gac atc      432
Asn Ala Ser Ser Lys Glu Ile Lys Thr Val Glu Ser Ile Thr Asp Ile
    130                 135                 140

agg gca gat ata gat aaa aaa tac aga tgt gtt agt ggc acc cag gtc      480
Arg Ala Asp Ile Asp Lys Lys Tyr Arg Cys Val Ser Gly Thr Gln Val
145                 150                 155                 160

cac atg aac aac gtg acc gta acg ctc cat gat gcc acc atc cag gcg      528
His Met Asn Asn Val Thr Val Thr Leu His Asp Ala Thr Ile Gln Ala
                165                 170                 175

tac ctt tcc aac agc agc ttc agc cgg gga gag aca cgc tgt gaa caa      576
Tyr Leu Ser Asn Ser Ser Phe Ser Arg Gly Glu Thr Arg Cys Glu Gln
            180                 185                 190

gac agg cct tcc cca acc aca gcg ccc cct gcg cca ccc agc ccc tcg      624
Asp Arg Pro Ser Pro Thr Thr Ala Pro Pro Ala Pro Pro Ser Pro Ser
        195                 200                 205

ccc tca ccc gtg ccc aag agc ccc tct gtg gac aag tac aac gtg agc      672
Pro Ser Pro Val Pro Lys Ser Pro Ser Val Asp Lys Tyr Asn Val Ser
    210                 215                 220

ggc acc aac ggg acc tgc ctg ctg gcc agc atg ggg ctg cag ctg aac      720
Gly Thr Asn Gly Thr Cys Leu Leu Ala Ser Met Gly Leu Gln Leu Asn
225                 230                 235                 240

ctc acc tat gag agg aag gac aac acg acg gtg aca agg ctt ctc aac      768
Leu Thr Tyr Glu Arg Lys Asp Asn Thr Thr Val Thr Arg Leu Leu Asn
                245                 250                 255

atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
            260                 265                 270

gtg act ctg gag ctg cac agc gag ggc acc acc gtc ctg ctc ttc cag      864
Val Thr Leu Glu Leu His Ser Glu Gly Thr Thr Val Leu Leu Phe Gln
        275                 280                 285

ttc ggg atg aat gca agt tct agc cgg ttt ttc cta caa gga atc cag      912
Phe Gly Met Asn Ala Ser Ser Ser Arg Phe Phe Leu Gln Gly Ile Gln
    290                 295                 300

ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320

aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
                325                 330                 335

tgc aac gcg gag gag cac gtc cgt gtc acg aag gcg ttt tca gtc aat     1056
Cys Asn Ala Glu Glu His Val Arg Val Thr Lys Ala Phe Ser Val Asn
            340                 345                 350

ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
```

-continued

```
        355                 360                 365

ggc tct gtg gag gag tgt ctg ctg gac gag aac agc ctc gag act aac      1152
Gly Ser Val Glu Glu Cys Leu Leu Asp Glu Asn Ser Leu Glu Thr Asn
    370                 375                 380

gca tgc tcc att aac ggt aat gct ccc gcc gag att gat ctg cgc caa      1200
Ala Cys Ser Ile Asn Gly Asn Ala Pro Ala Glu Ile Asp Leu Arg Gln
385                 390                 395                 400

atg aga acc gtt aca ccc ata agg tca gga gta gcc gct acg gaa tca      1248
Met Arg Thr Val Thr Pro Ile Arg Ser Gly Val Ala Ala Thr Glu Ser
                405                 410                 415

gca tac ctg gct tac aga aac cag tct ctg gac ctt gca gaa cag gaa      1296
Ala Tyr Leu Ala Tyr Arg Asn Gln Ser Leu Asp Leu Ala Glu Gln Glu
            420                 425                 430

ctg gtg gac tgc gca tca cag cac aac gga tgt cac ggg gac acc ata      1344
Leu Val Asp Cys Ala Ser Gln His Asn Gly Cys His Gly Asp Thr Ile
        435                 440                 445

ccc aga ggg atc gag tat atc cag cac aat ggc gta gtg cag gaa agc      1392
Pro Arg Gly Ile Glu Tyr Ile Gln His Asn Gly Val Val Gln Glu Ser
    450                 455                 460

tac tat agg tat gtc gcg cga gag caa agc tgt agg cgc cct aac gca      1440
Tyr Tyr Arg Tyr Val Ala Arg Glu Gln Ser Cys Arg Arg Pro Asn Ala
465                 470                 475                 480

cag cgt ttc gga atc tcc aat tac tgc cag atc tat ccg caa aac gtt      1488
Gln Arg Phe Gly Ile Ser Asn Tyr Cys Gln Ile Tyr Pro Gln Asn Val
                485                 490                 495

aac aaa atc cgt gaa gca ctg gcc caa acc cat agc gcc ata gct gtc      1536
Asn Lys Ile Arg Glu Ala Leu Ala Gln Thr His Ser Ala Ile Ala Val
            500                 505                 510

atc atc ggt atc aaa gat ctg gat gcc ttt cgg cac tac gat gga agg      1584
Ile Ile Gly Ile Lys Asp Leu Asp Ala Phe Arg His Tyr Asp Gly Arg
        515                 520                 525

act att ata cag cgc gac aat ggg tac cag ccc aat tat cac gca gtg      1632
Thr Ile Ile Gln Arg Asp Asn Gly Tyr Gln Pro Asn Tyr His Ala Val
    530                 535                 540

aac att gtg gga tat agc aat gcg caa ggt gtc gat tac tgg atc gtc      1680
Asn Ile Val Gly Tyr Ser Asn Ala Gln Gly Val Asp Tyr Trp Ile Val
545                 550                 555                 560

cgc aac tcc tgg gac aca aat tgg ggc gac aat ggc tat ggc tac ttt      1728
Arg Asn Ser Trp Asp Thr Asn Trp Gly Asp Asn Gly Tyr Gly Tyr Phe
                565                 570                 575

gct gcc aat att gac ctc atg atg ata gag gag tat ccg tac gtc gtg      1776
Ala Ala Asn Ile Asp Leu Met Met Ile Glu Glu Tyr Pro Tyr Val Val
            580                 585                 590

atc ctt ggc ggc ggc gga gat cag gta gac gtt aag gat tgc gct aac      1824
Ile Leu Gly Gly Gly Gly Asp Gln Val Asp Val Lys Asp Cys Ala Asn
        595                 600                 605

cat gag atc aag aaa gtc ttg gtg cca ggc tgt cat ggc tct gag cct      1872
His Glu Ile Lys Lys Val Leu Val Pro Gly Cys His Gly Ser Glu Pro
    610                 615                 620

tgc att atc cat cgc ggg aag cct ttt cag ctt gaa gcc gtc ttt gaa      1920
Cys Ile Ile His Arg Gly Lys Pro Phe Gln Leu Glu Ala Val Phe Glu
625                 630                 635                 640

gcc aac cag aac acc aag acg gcc aaa atc gag atc aag gct agc att      1968
Ala Asn Gln Asn Thr Lys Thr Ala Lys Ile Glu Ile Lys Ala Ser Ile
                645                 650                 655

gat ggg ctg gaa gtc gac gtt cca ggc att gac cca aac gcc tgt cac      2016
Asp Gly Leu Glu Val Asp Val Pro Gly Ile Asp Pro Asn Ala Cys His
            660                 665                 670

tac atg aag tgc cct ctg gtg aaa ggg cag cag tac gac ata aag tac      2064
```

-continued

```
Tyr Met Lys Cys Pro Leu Val Lys Gly Gln Gln Tyr Asp Ile Lys Tyr
        675                 680                 685

acc tgg aat gtg cct aaa atc gcc cca aaa tct gag aat gtg gtg gtt      2112
Thr Trp Asn Val Pro Lys Ile Ala Pro Lys Ser Glu Asn Val Val Val
    690                 695                 700

aca gtg aaa gtg atg ggc gat gac gga gtt ttg gcc tgt gcc ata gca      2160
Thr Val Lys Val Met Gly Asp Asp Gly Val Leu Ala Cys Ala Ile Ala
705                 710                 715                 720

acc cat gct aag att agg gac ggc ggt ggt ggg gcg aat gat aac gat      2208
Thr His Ala Lys Ile Arg Asp Gly Gly Gly Gly Ala Asn Asp Asn Asp
                725                 730                 735

gac gac ccc aca act act gta cat cct acc acc aca gaa caa ccg gat      2256
Asp Asp Pro Thr Thr Thr Val His Pro Thr Thr Thr Glu Gln Pro Asp
            740                 745                 750

gat aag ttt gaa tgc cca agc aga ttc ggt tat ttc gcg gat cca aag      2304
Asp Lys Phe Glu Cys Pro Ser Arg Phe Gly Tyr Phe Ala Asp Pro Lys
        755                 760                 765

gat cct cac aag ttc tac att tgc tca aac tgg gag gca gtg cat aaa      2352
Asp Pro His Lys Phe Tyr Ile Cys Ser Asn Trp Glu Ala Val His Lys
    770                 775                 780

gac tgt ccc ggc aat act cgg tgg aat gag gac gag gaa act tgt acc      2400
Asp Cys Pro Gly Asn Thr Arg Trp Asn Glu Asp Glu Glu Thr Cys Thr
785                 790                 795                 800

ggc ggt gga gga gat cca atc cac tat gac aag ata aca gaa gaa atc      2448
Gly Gly Gly Gly Asp Pro Ile His Tyr Asp Lys Ile Thr Glu Glu Ile
                805                 810                 815

aat aag gct gtg gat gag gct gtt gcc gcc atc gaa aag tcc gag aca      2496
Asn Lys Ala Val Asp Glu Ala Val Ala Ala Ile Glu Lys Ser Glu Thr
            820                 825                 830

ttc gat ccc atg aaa gtc ccc gac cac agc gac aag ttt gaa cgg cac      2544
Phe Asp Pro Met Lys Val Pro Asp His Ser Asp Lys Phe Glu Arg His
        835                 840                 845

att gga att atc gac ctg aaa ggg gaa ctc gac atg cgg aac att cag      2592
Ile Gly Ile Ile Asp Leu Lys Gly Glu Leu Asp Met Arg Asn Ile Gln
    850                 855                 860

gtt aga ggc ctc aaa cag atg aaa cga gtt ggg gat gct aat gtg aag      2640
Val Arg Gly Leu Lys Gln Met Lys Arg Val Gly Asp Ala Asn Val Lys
865                 870                 875                 880

agt gag gat ggg gtg gtg aag gca cat ctg ctc gta ggg gtc cat gac      2688
Ser Glu Asp Gly Val Val Lys Ala His Leu Leu Val Gly Val His Asp
                885                 890                 895

gat gtg gtc agt atg gag tat gat ctg gcc tac aaa ctc ggt gat ttg      2736
Asp Val Val Ser Met Glu Tyr Asp Leu Ala Tyr Lys Leu Gly Asp Leu
            900                 905                 910

cac ccc aat aca cac gta atc agt gac att cag gac ttt gtg gtg gag      2784
His Pro Asn Thr His Val Ile Ser Asp Ile Gln Asp Phe Val Val Glu
        915                 920                 925

ctg tct ctg gaa gtt tcc gag gag gga aac atg acc ctg act tcc ttc      2832
Leu Ser Leu Glu Val Ser Glu Glu Gly Asn Met Thr Leu Thr Ser Phe
    930                 935                 940

gag gtg cga cag ttc gca aac gtc gtg aat cac att gga ggc ctg tct      2880
Glu Val Arg Gln Phe Ala Asn Val Val Asn His Ile Gly Gly Leu Ser
945                 950                 955                 960

att ctg gat cct atc ttt gcc gtg ttg agt gac gtg ctg aca gcg atc      2928
Ile Leu Asp Pro Ile Phe Ala Val Leu Ser Asp Val Leu Thr Ala Ile
                965                 970                 975

ttc caa gac acg gtc aga gcc gag atg acc aaa gtg ctc gct cca gcc      2976
Phe Gln Asp Thr Val Arg Ala Glu Met Thr Lys Val Leu Ala Pro Ala
            980                 985                 990
```

```
ttc aag aag gag ctt gag cgg aac  aac cag gaa ttc acg  ctg atc ccc   3024
Phe Lys Lys Glu Leu Glu Arg Asn  Asn Gln Glu Phe Thr  Leu Ile Pro
        995               1000                 1005

atc gct  gtg ggt ggt gcc ctg  gcg ggg ctg gtc ctc  atc gtc ctc      3069
Ile Ala  Val Gly Gly Ala Leu  Ala Gly Leu Val Leu  Ile Val Leu
    1010                1015                1020

atc gcc  tac ctc gtc ggc agg  aag agg agt cac gca  ggc tac cag      3114
Ile Ala  Tyr Leu Val Gly Arg  Lys Arg Ser His Ala  Gly Tyr Gln
    1025                1030                1035

act atc  tag                                                        3123
Thr Ile
    1040


<210> SEQ ID NO 2
<211> LENGTH: 1040
<212> TYPE: PRT
<213> ORGANISM: Artificial Sequence
<220> FEATURE:
<223> OTHER INFORMATION: Synthetic Construct

<400> SEQUENCE: 2

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285
```

-continued

```
Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Thr Asn
    370                 375                 380

Ala Cys Ser Ile Asn Gly Asn Ala Pro Ala Glu Ile Asp Leu Arg Gln
385                 390                 395                 400

Met Arg Thr Val Thr Pro Ile Arg Ser Gly Val Ala Ala Thr Glu Ser
                405                 410                 415

Ala Tyr Leu Ala Tyr Arg Asn Gln Ser Leu Asp Leu Ala Glu Gln Glu
            420                 425                 430

Leu Val Asp Cys Ala Ser Gln His Asn Gly Cys His Gly Asp Thr Ile
        435                 440                 445

Pro Arg Gly Ile Glu Tyr Ile Gln His Asn Gly Val Val Gln Glu Ser
    450                 455                 460

Tyr Tyr Arg Tyr Val Ala Arg Glu Gln Ser Cys Arg Arg Pro Asn Ala
465                 470                 475                 480

Gln Arg Phe Gly Ile Ser Asn Tyr Cys Gln Ile Tyr Pro Gln Asn Val
                485                 490                 495

Asn Lys Ile Arg Glu Ala Leu Ala Gln Thr His Ser Ala Ile Ala Val
            500                 505                 510

Ile Ile Gly Ile Lys Asp Leu Asp Ala Phe Arg His Tyr Asp Gly Arg
        515                 520                 525

Thr Ile Ile Gln Arg Asp Asn Gly Tyr Gln Pro Asn Tyr His Ala Val
    530                 535                 540

Asn Ile Val Gly Tyr Ser Asn Ala Gln Gly Val Asp Tyr Trp Ile Val
545                 550                 555                 560

Arg Asn Ser Trp Asp Thr Asn Trp Gly Asp Asn Gly Tyr Gly Tyr Phe
                565                 570                 575

Ala Ala Asn Ile Asp Leu Met Met Ile Glu Glu Tyr Pro Tyr Val Val
            580                 585                 590

Ile Leu Gly Gly Gly Gly Asp Gln Val Asp Val Lys Asp Cys Ala Asn
        595                 600                 605

His Glu Ile Lys Lys Val Leu Val Pro Gly Cys His Gly Ser Glu Pro
    610                 615                 620

Cys Ile Ile His Arg Gly Lys Pro Phe Gln Leu Glu Ala Val Phe Glu
625                 630                 635                 640

Ala Asn Gln Asn Thr Lys Thr Ala Lys Ile Glu Ile Lys Ala Ser Ile
                645                 650                 655

Asp Gly Leu Glu Val Asp Val Pro Gly Ile Asp Pro Asn Ala Cys His
            660                 665                 670

Tyr Met Lys Cys Pro Leu Val Lys Gly Gln Gln Tyr Asp Ile Lys Tyr
        675                 680                 685

Thr Trp Asn Val Pro Lys Ile Ala Pro Lys Ser Glu Asn Val Val Val
    690                 695                 700
```

-continued

```
Thr Val Lys Val Met Gly Asp Asp Gly Val Leu Ala Cys Ala Ile Ala
705                 710                 715                 720

Thr His Ala Lys Ile Arg Asp Gly Gly Gly Gly Ala Asn Asp Asn Asp
                725                 730                 735

Asp Asp Pro Thr Thr Thr Val His Pro Thr Thr Thr Glu Gln Pro Asp
            740                 745                 750

Asp Lys Phe Glu Cys Pro Ser Arg Phe Gly Tyr Phe Ala Asp Pro Lys
        755                 760                 765

Asp Pro His Lys Phe Tyr Ile Cys Ser Asn Trp Glu Ala Val His Lys
    770                 775                 780

Asp Cys Pro Gly Asn Thr Arg Trp Asn Glu Asp Glu Glu Thr Cys Thr
785                 790                 795                 800

Gly Gly Gly Gly Asp Pro Ile His Tyr Asp Lys Ile Thr Glu Glu Ile
                805                 810                 815

Asn Lys Ala Val Asp Glu Ala Val Ala Ala Ile Glu Lys Ser Glu Thr
            820                 825                 830

Phe Asp Pro Met Lys Val Pro Asp His Ser Asp Lys Phe Glu Arg His
        835                 840                 845

Ile Gly Ile Ile Asp Leu Lys Gly Glu Leu Asp Met Arg Asn Ile Gln
    850                 855                 860

Val Arg Gly Leu Lys Gln Met Lys Arg Val Gly Asp Ala Asn Val Lys
865                 870                 875                 880

Ser Glu Asp Gly Val Val Lys Ala His Leu Leu Val Gly Val His Asp
                885                 890                 895

Asp Val Val Ser Met Glu Tyr Asp Leu Ala Tyr Lys Leu Gly Asp Leu
            900                 905                 910

His Pro Asn Thr His Val Ile Ser Asp Ile Gln Asp Phe Val Val Glu
        915                 920                 925

Leu Ser Leu Glu Val Ser Glu Glu Gly Asn Met Thr Leu Thr Ser Phe
    930                 935                 940

Glu Val Arg Gln Phe Ala Asn Val Val Asn His Ile Gly Gly Leu Ser
945                 950                 955                 960

Ile Leu Asp Pro Ile Phe Ala Val Leu Ser Asp Val Leu Thr Ala Ile
                965                 970                 975

Phe Gln Asp Thr Val Arg Ala Glu Met Thr Lys Val Leu Ala Pro Ala
            980                 985                 990

Phe Lys Lys Glu Leu Glu Arg Asn  Asn Gln Glu Phe Thr  Leu Ile Pro
        995                 1000                1005

Ile Ala  Val Gly Gly Ala Leu  Ala Gly Leu Val Leu  Ile Val Leu
    1010                1015                1020

Ile Ala  Tyr Leu Val Gly Arg  Lys Arg Ser His Ala  Gly Tyr Gln
    1025                1030                1035

Thr Ile
    1040


<210> SEQ ID NO 3
<211> LENGTH: 6127
<212> TYPE: DNA
<213> ORGANISM: Artificial Sequence
<220> FEATURE:
<223> OTHER INFORMATION: A vector comprising nucleic acid encoding a
      chimeric protein

<400> SEQUENCE: 3

ccgcctaatg agcgggcttt tttttcttag ggtgcaaaag gagagcctgt aagcgggcac     60
```

-continued

```
tcttccgtgg tctggtggat aaattcgcaa gggtatcatg gcggacgacc ggggttcgag    120
ccccgtatcc ggccgtccgc cgtgatccat gcggttaccg cccgcgtgtc gaacccaggt    180
gtgcgacgtc agacaacggg ggagtgctcc ttttggcttc cttccccttc ttccgcttcc    240
tcgctcactg actcgctgcg ctcggtcgtt cggctgcggc gagcggtatc agctcactca    300
aaggcggtaa tacggttatc cacagaatca ggggataacg caggaaagaa catgtgagca    360
aaaggccagc aaaaggccag gaaccgtaaa aaggccgcgt tgctggcgtt tttccatagg    420
ctccgccccc ctgacgagca tcacaaaaat cgacgctcaa gtcagaggtg gcgaaacccg    480
acaggactat aaagatacca ggcgtttccc cctggaagct ccctcgtgcg ctctcctgtt    540
ccgaccctgc cgcttaccgg atacctgtcc gcctttctcc cttcgggaag cgtggcgctt    600
tctcatagct cacgctgtag gtatctcagt tcggtgtagg tcgttcgctc caagctgggc    660
tgtgtgcacg aaccccccgt tcagcccgac cgctgcgcct tatccggtaa ctatcgtctt    720
gagtccaacc cggtaagaca cgacttatcg ccactggcag cagccactgg taacaggatt    780
agcagagcga ggtatgtagg cggtgctaca gagttcttga agtggtggcc taactacggc    840
tacactagaa gaacagtatt tggtatctgc gctctgctga agccagttac cttcggaaaa    900
agagttggta gctcttgatc cggcaaacaa accaccgctg gtagcggtgg tttttttgtt    960
tgcaagcagc agattacgcg cagaaaaaaa ggatctcaag aagatccttt gatcttttct   1020
acggggtctg acgctcagtg gaacgaaaac tcacgttaag ggattttggt catgagatta   1080
tcaaaaagga tcttcaccta gatcctttta aattaaaaat gaagttttaa atcaatctaa   1140
agtatatatg agtaaacttg gtctgacagt taccaatgct taatcagtga ggcacctatc   1200
tcagcgatct gtctatttcg ttcatccata gttgcctgac tcctgcaaac cacgttgtgg   1260
tagaattggt aaagagagtc gtgtaaaata tcgagttcgc acatcttgtt gtctgattat   1320
tgatttttgg cgaaaccatt tgatcatatg acaagatgtg tatctacctt aacttaatga   1380
ttttgataaa aatcattagg taccccggct ctagatggca tgacattaac ctataaaaat   1440
aggcgtatca cgaggccctt tcgtctcgcg cgtttcggtg atgacggtga aaacctctga   1500
cacatgcagc tcccggagac ggtcacagct tgtctgtaag cggatgccgg gagcagacaa   1560
gcccgtcagg gcgcgtcagc gggtgttggc gggtgtcggg gctggcttaa ctatgcggca   1620
tcagagcaga ttgtactgag agtgcaccat atgcggtgtg aaataccgca cagatgcgta   1680
aggagaaaat accgcatcag attggctatt ggccattgca tacgttgtat ccatatcata   1740
atatgtacat ttatattggc tcatgtccaa cattaccgcc atgttgacat tgattattga   1800
ctagttatta atagtaatca attacggggt cattagttca tagcccatat atggagttcc   1860
gcgttacata acttacggta aatggcccgc ctggctgacc gcccaacgac ccccgcccat   1920
tgacgtcaat aatgacgtat gttcccatag taacgccaat agggactttc cattgacgtc   1980
aatgggtgga gtatttacgg taaactgccc acttggcagt acatcaagtg tatcatatgc   2040
caagtacgcc ccctattgac gtcaatgacg gtaaatggcc cgcctggcat tatgcccagt   2100
acatgacctt atgggacttt cctacttggc agtacatcta cgtattagtc atcgctatta   2160
ccatggtgat gcggttttgg cagtacatca atgggcgtgg atagcggttt gactcacggg   2220
gatttccaag tctccacccc attgacgtca atgggagttt gttttggcac caaaatcaac   2280
gggactttcc aaaatgtcgt aacaactccg ccccattgac gcaaatgggc ggtaggcgtg   2340
tacggtggga ggtctatata agcagagctc gtttagtgaa ccgtcagatc gcctggagac   2400
gccatccacg ctgttttgac ctccatagaa gacaccggga ccgatccagc ctccgcggct   2460
```

```
cgcatctctc cttcacgcgc ccgccgccct acctgaggcc gccatccacg ccggttgagt   2520
cgcgttctgc cgcctcccgc ctgtggtgcc tcctgaactg cgtccgccgt ctaggtaagt   2580
ttaaagctca ggtcgagacc gggcctttgt ccggcgctcc cttggagcct acctagactc   2640
agccggctct ccacgctttg cctgaccctg cttgctcaac tctagttctc tcgttaactt   2700
aatgagacag atagaaactg gtcttgtaga aacagagtag tcgcctgctt ttctgccagg   2760
tgctgacttc tctcccctgg gctttttttct tttctcagg ttgaaaagaa gaagacgaag   2820
aagacgaaga agacaaaccg tcgtcgacat ggcgccccgc agcgcccggc gacccctgct   2880
gctgctactg ctgttgctgc tgctcggcct catgcattgt gcgtcagcag caatgtttat   2940
ggtgaaaaat ggcaacggga ccgcgtgcat aatggccaac ttctctgctg ccttctcagt   3000
gaactacgac accaagagtg gccctaagaa catgaccctt gacctgccat cagatgccac   3060
agtggtgctc aaccgcagct cctgtggaaa agagaacact tctgacccca gtctcgtgat   3120
tgcttttgga agaggacata cactcactct caatttcacg agaaatgcaa cacgttacag   3180
cgtccagctc atgagtttg tttataactt gtcagacaca cacctttcc ccaatgcgag     3240
ctccaaagaa atcaagactg tggaatctat aactgacatc agggcagata tagataaaaa   3300
atacagatgt gttagtggca cccaggtcca catgaacaac gtgaccgtaa cgctccatga   3360
tgccaccatc caggcgtacc tttccaacag cagcttcagc cggggagaga cacgctgtga   3420
acaagacagg ccttccccaa ccacagcgcc ccctgcgcca cccagcccct cgccctcacc   3480
cgtgcccaag agcccctctg tggacaagta caacgtgagc ggcaccaacg ggacctgcct   3540
gctggccagc atggggctgc agctgaacct cacctatgag aggaaggaca acacgacggt   3600
gacaaggctt ctcaacatca accccaacaa gacctcggcc agcgggagct gcggcgccca   3660
cctggtgact ctggagctgc acagcgaggg caccaccgtc ctgctcttcc agttcgggat   3720
gaatgcaagt tctagccggt tttcctaca aggaatccag ttgaatacaa ttcttcctga    3780
cgccagagac cctgccttta aagctgccaa cggctccctg cgagcgctgc aggccacagt   3840
cggcaattcc tacaagtgca acgcggagga gcacgtccgt gtcacgaagg cgttttcagt   3900
caatatattc aaagtgtggg tccaggcttt caaggtggaa ggtggccagt ttggctctgt   3960
ggaggagtgt ctgctggacg agaacagcct cgagactaac gcatgctcca ttaacggtaa   4020
tgctcccgcc gagattgatc tgcgccaaat gagaaccgtt acacccataa ggtcaggagt   4080
agccgctacg gaatcagcat acctggctta cagaaaccag tctctggacc ttgcagaaca   4140
ggaactggtg gactgcgcat cacagcacaa cggatgtcac ggggacacca tacccagagg   4200
gatcgagtat atccagcaca atggcgtagt gcaggaaagc tactataggt atgtcgcgcg   4260
agagcaaagc tgtaggcgcc ctaacgcaca gcgtttcgga atctccaatt actgccagat   4320
ctatccgcaa aacgttaaca aaatccgtga agcactggcc caaacccata gcgccatagc   4380
tgtcatcatc ggtatcaaag atctggatgc ctttcggcac tacgatggaa ggactattat   4440
acagcgcgac aatgggtacc agcccaatta tcacgcagtg aacattgtgg gatatagcaa   4500
tgcgcaaggt gtcgattact ggatcgtccg caactcctgg gacacaaatt ggggcgacaa   4560
tggctatggc tactttgctg ccaatattga cctcatgatg atagaggagt atccgtacgt   4620
cgtgatcctt ggcggcggcg gagatcaggt agacgttaag gattgcgcta accatgagat   4680
caagaaagtc ttggtgccag gctgtcatgg ctctgagcct tgcattatcc atcgcgggaa   4740
gccttttcag cttgaagccg tctttgaagc caaccagaac accaagacgg ccaaaatcga   4800
```

-continued

```
gatcaaggct agcattgatg ggctggaagt cgacgttcca ggcattgacc caaacgcctg   4860
tcactacatg aagtgccctc tggtgaaagg gcagcagtac gacataaagt acacctggaa   4920
tgtgcctaaa atcgccccaa aatctgagaa tgtggtggtt acagtgaaag tgatgggcga   4980
tgacggagtt ttggcctgtg ccatagcaac ccatgctaag attagggacg gcggtggtgg   5040
ggcgaatgat aacgatgacg accccacaac tactgtacat cctaccacca cagaacaacc   5100
ggatgataag tttgaatgcc caagcagatt cggttatttc gcggatccaa aggatcctca   5160
caagttctac atttgctcaa actgggaggc agtgcataaa gactgtcccg gcaatactcg   5220
gtggaatgag gacgaggaaa cttgtaccgg cggtggagga gatccaatcc actatgacaa   5280
gataacagaa gaaatcaata aggctgtgga tgaggctgtt gccgccatcg aaaagtccga   5340
gacattcgat cccatgaaag tccccgacca cagcgacaag tttgaacggc acattggaat   5400
tatcgacctg aaaggggaac tcgacatgcg gaacattcag gttagaggcc tcaaacagat   5460
gaaacgagtt ggggatgcta atgtgaagag tgaggatggg gtggtgaagg cacatctgct   5520
cgtaggggtc catgacgatg tggtcagtat ggagtatgat ctggcctaca aactcggtga   5580
tttgcacccc aatacacacg taatcagtga cattcaggac tttgtggtgg agctgtctct   5640
ggaagtttcc gaggagggaa acatgaccct gacttccttc gaggtgcgac agttcgcaaa   5700
cgtcgtgaat cacattggag gcctgtctat tctggatcct atctttgccg tgttgagtga   5760
cgtgctgaca gcgatcttcc aagacacggt cagagccgag atgaccaaag tgctcgctcc   5820
agccttcaag aaggagcttg agcggaacaa ccaggaattc acgctgatcc ccatcgctgt   5880
gggtggtgcc ctggcggggc tggtcctcat cgtcctcatc gcctacctcg tcggcaggaa   5940
gaggagtcac gcaggctacc agactatcta gtaaggatct ttttccctct gccaaaaatt   6000
atggggacat catgaagccc cttgagcatc tgacttctgg ctaataaagg aaatttattt   6060
tcattgcaat agtgtgttgg aattttttgt gtctctcact cggaaggaca taagggcggc   6120
cgctagc                                                             6127
```

NUCLEIC ACID FOR TREATING MITE ALLERGY

CROSS-REFERENCE TO RELATED APPLICATIONS

This application is a Continuation of U.S. application Ser. No. 17/054,340, filed Nov. 10, 2020, which is the U.S. National Stage application of PCT/JP2019/018657, filed May 10, 2019, which claims priority to JP 2018-091963, filed May 11, 2018. The entire contents of each of the aforementioned applications are incorporated herein by reference.

The instant application contains a Sequence Listing which has been submitted in ASCII format via EFS-WEB and is hereby incorporated by reference in its entirety. Said ASCII copy, created on Nov. 9, 2020, is named sequence.txt and is 32,768 bytes.

TECHNICAL FIELD

The present invention relates to a nucleic acid which is expected to be useful as an active ingredient of a pharmaceutical composition, for example, a nucleic acid which is expected to be useful for treating mite allergy.

BACKGROUND ART

Mite allergy is an allergic disease that occurs in response to mite-derived allergens. The allergic disease is caused by the following steps: 1) allergens taken into a body are phagocytosed by antigen-presenting cells and presented to naive T cells, 2) the naive T cells are differentiated into Th2 cells, 3) cytokine such as IL-4 is produced from an immune cell such as the Th2 cell, 4) B cells produce IgE by IL-4, and 5) IgE binding to the allergens binds to mast cells. It has been known that in allergic disease patients, antagonism between Th1-type immunity involving Th1 cells producing IFN-γ or the like and Th2-type immunity involving Th2 cells producing IL-4 or the like shifts to Th2-type dominant which results in Th2-type inflammatory immune response (Middleton's Allergy Seventh edition Principles & Practice, 2009). Thus, IFN-γ can be used as an indicator of Th1-type immunity, and IL-4 can be used as an indicator of Th2-type immunity. Further, in mice, IFN-γ causes a preferential class switch to IgG2a isotype in activated B cells, while suppresses responses to all the other isotypes. That is, IgG2a can also be used as an indicator of Th1-type immunity. For example, it has been known that production of IgG2a is promoted in IL-4-deficient mice and that IgG2a production is suppressed in IFN-γ-deficient mice (Arthritis Res., 2002, Vol. 4, p. 54-58). There is also a report that antibodies produced from B cells are involved in the mechanism of action of allergen immunotherapy. For example, it has been known that in humans, IgG antagonizes IgE binding to an allergen to inhibit formation of allergen-IgE complex and thereby inhibit histamine release from mast cells (J Allergy Clin Immunol., 2017, Vol. 140, p. 1485-1498).

Until now, development of multiple immunotherapies for mite allergy has been advanced (J Allergy Clin Immunol., 2013, Vol. 132, p. 1322-1336; WO 2014/195803; Expert Rev Vaccines., 2014, Vol. 13, p. 1427-1438). Further, Der p 1, Der p 2, Der p 7, Der p 23, and the like have been known as allergens related to the mite allergy (Patent Documents 1 and 2, and Non-Patent Document 1). However, for example, subcutaneous immunotherapy (SCIT) and sublingual immunotherapy (SLIT) have problems such as possibility of anaphylaxis and long treatment period over several years.

As one of the techniques for nucleic acid vaccines, nucleic acid vaccines for treating allergy using lysosome-associated membrane proteins (LAMP) have been studied.

Further, a plasmid comprising a nucleic acid encoding a chimeric protein comprising LAMP-1, which is a member of LAMP family, and Cry J1 and/or Cry J2, which are allergens of *Cryptomeria japonica*, was constructed (Patent Document 3 and Non-Patent Document 2). It has been reported that such a plasmid does not cause systemic release of free allergen which causes anaphylaxis, but induces a Th1-type immune response. Furthermore, it has been reported that a plasmid comprising a nucleic acid encoding a chimeric protein comprising LAMP-1 and peanut allergens Ara H1, Ara H2 and Ara H3 reduced production of IgE in a mouse model (Patent Document 4). In a field of mite allergy, a vaccine comprising a nucleic acid encoding a chimeric protein comprising Der p 1 and a transmembrane domain of LAMP-1 and an endosomal/lysosomal targeting domain has been constructed (Patent Document 5 and Non-Patent Document 3). However, a nucleic acid vaccine for treating mite allergy comprising multiple mite allergen antigens, and an intra-organelle stabilizing domain of LAMP-1 and an endosomal/lysosomal targeting domain has not been reported.

RELATED ART

Patent Document

[Patent Document 1] WO 1988/010297

[Patent Document 2] WO 2007/124524

[Patent Document 3] WO 2013/187906

[Patent Document 4] WO 2015/200357

[Patent Document 5] WO 2004/019978

Non-Patent Document

[Non-Patent Document 1] "Clinical & Experimental Allergy", (UK), 1995; 25: 416-422

[Non-Patent Document 2] "Journal of Immunology Research", (Egypt), 2016; Article ID 4857869

[Non-Patent Document 3] "Vaccine", (Netherlands), 2006; 24 (29-30): 5762-5771

SUMMARY OF INVENTION

Problems to Be Solved by the Invention

An object of the present invention is to provide a nucleic acid which is expected to be useful for treating mite allergy.

Means for Solving the Problems

As a result of repeated investigation with considerable creativity in the preparation of nucleic acids for treating mite allergy, the present inventors have prepared LAMP-Der p 1-Der p 2-Der p 23-Der p 7 plasmid (Example 1), confirmed that a chimeric protein is expressed from the plasmid (Example 2), and found that a Th1-type immune response is induced in mice to which the plasmid is administered (Examples 3 and 4). As a result, a nucleic acid which is expected to be useful for treating mite allergy is provided, and thereby the present invention has been completed.

That is, the present invention relates to the following [1] to [17].

[1]

A nucleic acid comprising:

a nucleotide sequence encoding a chimeric protein, wherein the nucleotide sequence is a nucleotide sequence comprising the following nucleotide sequences in this order:

a nucleotide sequence encoding a signal peptide;

a nucleotide sequence encoding an intra-organelle stabilizing domain of LAMP;

a nucleotide sequence encoding an allergen domain comprising Der p 1, Der p 2, Der p 23, and Der p 7;

a nucleotide sequence encoding a transmembrane domain; and a nucleotide sequence encoding an endosomal/lysosomal targeting domain of LAMP.

[2]

A nucleic acid comprising:

a nucleotide sequence encoding a chimeric protein, wherein the nucleotide sequence is a nucleotide sequence comprising the following nucleotide sequences in this order:

a nucleotide sequence encoding a signal peptide;

a nucleotide sequence encoding an intra-organelle stabilizing domain of LAMP;

a nucleotide sequence encoding an allergen domain comprising Der p 1, Der p 2, Der p 23, and Der p 7 in this order;

a nucleotide sequence encoding a transmembrane domain; and a nucleotide sequence encoding an endosomal/lysosomal targeting domain of LAMP.

[3]

The nucleic acid described in [1] or [2], wherein the signal peptide is a signal peptide of LAMP.

[4]

The nucleic acid described in any one of [1] to [3], wherein the transmembrane domain is a transmembrane domain of LAMP.

[5]

The nucleic acid described in any one of [1] to [4], wherein the signal peptide consists of the amino acid sequence of amino acid numbers 1 to 27 of SEQ ID NO: 2, the intra-organelle stabilizing domain consists of an amino acid sequence of amino acid numbers 28 to 380 of SEQ ID NO: 2, the allergen domain is an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, the transmembrane domain consists of the amino acid sequence of amino acid numbers 1006 to 1028 of SEQ ID NO: 2, and the endosomal/lysosomal targeting domain consists of the an amino acid sequence of amino acid numbers 1037 to 1040 of SEQ ID NO: 2.

[6]

A nucleic acid comprising:

a nucleotide sequence encoding a chimeric protein consisting of an amino acid sequence having at least 90% identity to the amino acid sequence shown by SEQ ID NO: 2, wherein the nucleic acid has an action of inducing Th1-type immunity to an allergen selected from the group consisting of Der p 1, Der p 2, Der p 23, and Der p 7.

[7]

A nucleic acid comprising:

a) a nucleotide sequence encoding a chimeric protein consisting of the amino acid sequence shown by SEQ ID NO: 2; or b) a nucleotide sequence encoding a chimeric protein consisting of an amino acid sequence in which 1 to 10 amino acids are deleted, substituted, inserted and/or added in the amino acid sequence shown by SEQ ID NO: 2, wherein the nucleic acid has an action of inducing Th1-type immunity to an allergen selected from the group consisting of Der p 1, Der p 2, Der p 23, and Der p 7.

[8]

A nucleic acid comprising:

a nucleotide sequence encoding a chimeric protein consisting of an amino acid sequence shown by SEQ ID NO: 2.

[9]

An expression vector comprising:

the nucleic described in any one of [1] to [8].

[10]

An expression vector comprising:

the nucleic acid described in [8].

A host cell transformed with the nucleic acid described in any one of [1] to [8].

[12]

A method for producing a nucleic acid, comprising: culturing a host cell transformed with the nucleic acid described in any one of [1] to [8].

[13]

A pharmaceutical composition comprising:

the expression vector described in [10] and a pharmaceutically acceptable excipient.

[14]

The pharmaceutical composition described in [13], which is a pharmaceutical composition for preventing or treating mite allergy.

[15]

A method for preventing or treating mite allergy, comprising:

administering a prophylactically effective or therapeutically effective amount of the expression vector described in [10].

[16]

The expression vector described in [10], for use in preventing or treating mite allergy.

Use of the expression vector described in [10] for the manufacture of a pharmaceutical composition for preventing or treating mite allergy.

Effects of the Invention

The nucleic acid of the present invention can be used for preventing or treating mite allergy.

EMBODIMENTS FOR CARRYING OUT THE INVENTION

Figure 1:
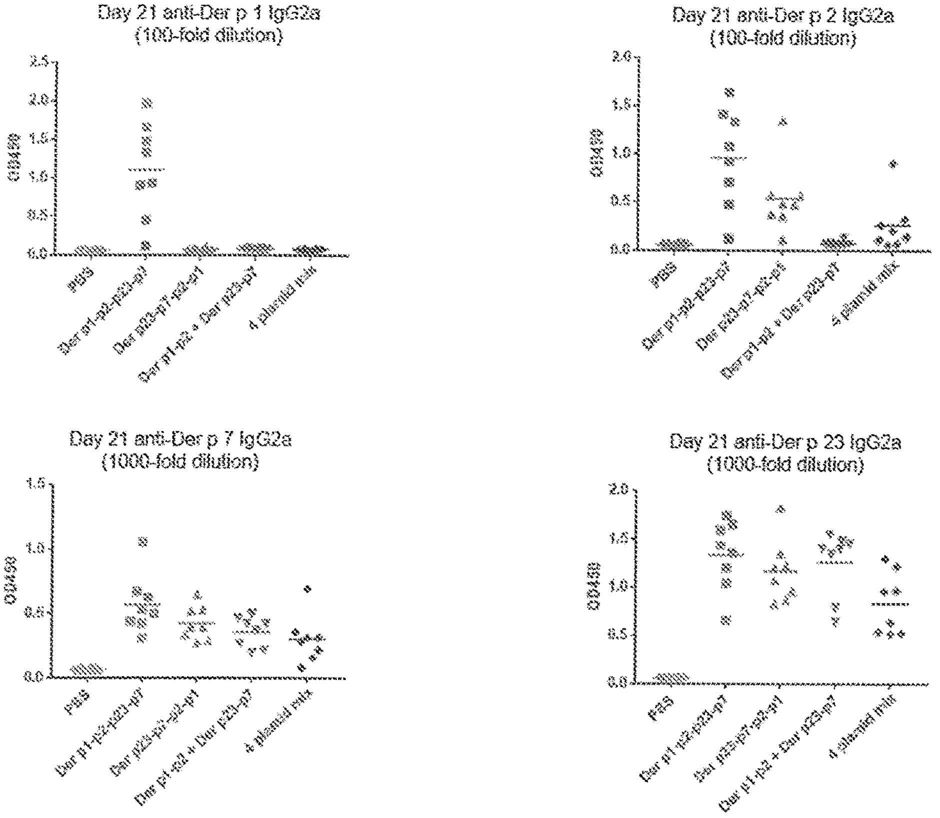
FIG. 1 is a diagram illustrating production of IgG2a specific to Der p 1, Der p 2, Der p 23, and Der p 7, which is induced when the nucleic acid of the present invention is administered to a mouse. The vertical axis indicates absorbance at 450 nm, and the horizontal axis indicates each administration group. The horizontal lines indicate arithmetic mean values.

Hereinafter, the present invention will be described in detail.

<Nucleic Acid of the Present Invention>

Examples of the nucleic acid of the present invention include a nucleic acid having the following features:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide, a nucleotide sequence encoding an intra-organelle stabilizing domain of LAMP, a nucleotide sequence encoding an allergen domain comprising Der p 1, Der p 2, Der p 23, and Der p 7, a nucleotide sequence encoding a transmembrane domain, and a nucleotide sequence encoding an endosomal/lysosomal targeting domain of LAMP.

In the present invention, the nucleic acid is a polymer which is formed by polymerization of nucleotides and consists of a nucleotide sequence with an arbitrary length. The nucleotides can include deoxyribonucleotides, ribonucleotides, and/or their analogs. The nucleic acid of the present invention is DNA, RNA or modified a nucleic acid thereof. In one embodiment, the nucleic acid of the present invention is DNA.

In one embodiment, the nucleic acid of the present invention is a nucleic acid introduced into an expression vector. In one embodiment, the nucleic acid of the present invention is a nucleic acid introduced into a plasmid vector.

In the specification, "chimeric protein" means a protein encoded by a nucleotide sequence in which two or more genes are fused by using genetic recombination technology. The nucleic acid of the present invention includes a nucleotide sequence encoding chimeric protein comprising a signal peptide, an intra-organelle stabilizing domain of LAMP, an allergen domain comprising Der p 1, Der p 2, Der p 23, and Der p 7, a transmembrane domain, and an endosomal/lysosomal targeting domain of LAMP in this order (hereinafter, referred to as "chimeric protein relating to the present invention").

LAMP is well-known protein to those skilled in the art (J Biol Chem., 1991, Vol.266, p.21327-21330). In the present specification, LAMP is not particularly limited, but examples thereof include LAMP-1, LAMP-2, CD63/LAMP-3, DC-LAMP, and LIMP II, and homologs, orthologs, paralogs, variants, and modified proteins thereof. In one embodiment of the present invention, LAMP is LAMP-1. In the present invention, an animal from which LAMP is derived is not particularly limited, but in one embodiment, LAMP is human LAMP. In one embodiment, human LAMP is human LAMP-1. Examples of an amino acid sequence of human LAMP-1 include an amino acid sequence in which the amino acid sequence shown by amino acid numbers 1005 to 1040 of SEQ ID NO: 2 is bound to a C-terminal of the amino acid sequence shown by amino acid numbers 1 to 380 of SEQ ID NO: 2.

The general structure of the signal peptide is well known to those skilled in the art (Annu Rev Biochem., 2003, Vol. 72, p. 395 to 447). The signal peptide has a function of directing transport and localization of a protein. As the signal peptide used in the present invention, any suitable signal peptide can be selected as long as it has a function of directing transport and localization of the protein. In one embodiment, the signal peptide used in the present invention is a signal peptide of LAMP. In one embodiment, the signal peptide of LAMP used in the present invention is a signal peptide of LAMP-1.

In one embodiment, the signal peptide used in the present invention consists of the following amino acid sequence of (a) or (b):

(a) an amino acid sequence having at least 90% identity to the amino acid sequence of amino acid numbers 1 to 27 of SEQ ID NO: 2; or (b) the amino acid sequence of amino acid numbers 1 to 27 of SEQ ID NO: 2, or an amino acid sequence in which 1 to 3 amino acids are deleted, substituted, inserted and/or added in the amino acid sequence of amino acid numbers 1 to 27 of SEQ ID NO: 2.

The term of "identity" in the present specification means a value of Identity obtained by using an EMBOSS Needle (Nucleic Acids Res., 2015, Vol. 43, p.W580-W584; ebi-.ac.uk/Tools/psa/emboss needle/) with a parameter prepared by default.

The above parameters are as follows.

Gap Open Penalty=10

Gap Extend Penalty=0.5

Matrix=EBLOSUM62

End Gap Penalty=false

In one embodiment, the signal peptide used in the present invention consists of the amino acid sequence of amino acid numbers 1 to 27 of SEQ ID NO: 2.

The sequence of the intra-organelle stabilizing domain of LAMP is well known to those skilled in the art (WO 2013/187906). The intra-organelle stabilizing domain of LAMP has a function of protecting the allergen domain from proteases, low pH, and other substances and conditions that destabilize a protein. As the intra-organelle stabilizing domain of LAMP used in the present invention, any suitable intra-organelle stabilizing domain of LAMP can be selected as long as it has a function of protecting the allergen domain from proteases, low pH, and other substances and conditions that destabilize a protein. In one embodiment, the intra-organelle stabilizing domain of LAMP used in the present invention is an intra-organelle stabilizing domain of LAMP-1.

In one embodiment, the intra-organelle stabilizing domain of LAMP used in the present invention consists of the following amino acid sequence of (a) or (b):

(a) an amino acid sequence having at least 90% identity to the amino acid sequence of amino acid numbers 28 to 380 of SEQ ID NO: 2; or (b) the amino acid sequence of amino acid numbers 28 to 380 of SEQ ID NO: 2, or an amino acid sequence in which 1 to 10 amino acids are deleted, substituted, inserted and/or added in the amino acid sequence of amino acid numbers 28 to 380 of SEQ ID NO: 2.

In one embodiment, the intra-organelle stabilizing domain of LAMP used in the present invention consists of the amino acid sequence of amino acid numbers 28 to 380 of SEQ ID NO: 2.

The allergen domain used in the present invention includes Der p 1, Der p 2, Der p 23, and Der p 7 as allergens. Der p 1, Der p 2, Der p 23, and Der p 7 are allergens that can be observed in mites (WO 1988/010297; WO 2007/124524; and Clin Exp Allergy., 1995, Vol. 25, p. 416-422). Der p 1, Der p 2, Der p 23, and Der p 7 used in the present invention may be variants thereof as long as they have antigenicity. The antigenicity of any protein can be confirmed, for example, by observing that administration to an animal elicits antibody production or T cell response to that protein (Bioanalysis., 2012, Vol. 4, p. 397-406). In one embodiment, Der p 1, Der p 2, Der p 23, and Der p 7 used in the present invention lack the signal peptide.

In one embodiment, Der p 1 consists of the following amino acid sequence of (a) or (b):

(a) an amino acid sequence having at least 90% identity to the amino acid sequence of amino acid numbers 383 to 594 of SEQ ID NO: 2; or (b) the amino acid sequence of amino acid numbers 383 to 594 of SEQ ID NO: 2, or an amino acid sequence in which 1 to 10 amino acids are deleted, substituted, inserted and/or added in the amino acid sequence of amino acid numbers 383 to 594 of SEQ ID NO: 2.

In one embodiment, Der p 1 consists of the amino acid sequence of amino acid numbers 383 to 594 of SEQ ID NO: 2.

In one embodiment, Der p 2 consists of the following amino acid sequence of (a) or (b):

(a) an amino acid sequence having at least 90% identity to the amino acid sequence of amino acid numbers 599 to 727 of SEQ ID NO: 2; or (b) the amino acid sequence of amino acid numbers 599 to 727 of SEQ ID NO: 2, or an amino acid sequence in which 1 to 10 amino acids are deleted, substituted, inserted and/or added in the amino acid sequence of amino acid numbers 599 to 727 of SEQ ID NO: 2.

In one embodiment, Der p 2 consists of the amino acid sequence of amino acid numbers 599 to 727 of SEQ ID NO: 2.

In one embodiment, Der p 23 consists of the following amino acid sequence of (a) or (b):

(a) an amino acid sequence having at least 90% identity to the amino acid sequence of amino acid numbers 732 to 800 of SEQ ID NO: 2; or (b) the amino acid sequence of amino acid numbers 732 to 800 of SEQ ID NO: 2, or an amino acid sequence in which 1 to 10 amino acids are deleted, substituted, inserted and/or added in the amino acid sequence of amino acid numbers 732 to 800 of SEQ ID NO: 2.

In one embodiment, Der p 23 consists of the amino acid sequence of amino acid numbers 732 to 800 of SEQ ID NO: 2.

In one embodiment, Der p 7 consists of the following amino acid sequence of (a) or (b):

(a) an amino acid sequence having at least 90% identity to the amino acid sequence of amino acid numbers 805 to 1002 of SEQ ID NO: 2; or (b) the amino acid sequence of amino acid numbers 805 to 1002 of SEQ ID NO: 2, or an amino acid sequence in which 1 to 10 amino acids are deleted, substituted, inserted and/or added in the amino acid sequence of amino acid numbers 805 to 1002 of SEQ ID NO: 2.

In one embodiment, Der p 7 consists of the amino acid sequence of amino acid numbers 805 to 1002 of SEQ ID NO: 2.

In one embodiment, the allergen domain used in the present invention comprises Der p 1, Der p 2, Der p 23, and Der p 7 in any order. In addition, in one embodiment, the allergen domain used in the present invention comprises Der p 1, Der p 2, Der p 23, and Der p 7 in this order.

In one embodiment, the allergen domain used in the present invention consists of the amino acid sequence of amino acid numbers 383 to 1002 of SEQ ID NO: 2.

The general structure of the transmembrane domain is well known to those skilled in the art (Annu Rev Biochem., 2007, Vol. 76, p. 125 to 140). The transmembrane domain has a function of anchoring proteins to biological membranes. As the transmembrane domain used in the present invention, any suitable transmembrane domain protein can be selected as long as it has a function of anchoring proteins to biological membranes. In one embodiment, the transmembrane domain used in the present invention is a transmembrane domain of LAMP. In one embodiment, the transmembrane domain of LAMP used in the present invention is a transmembrane domain of LAMP-1.

In one embodiment, the transmembrane domain used in the present invention consists of the following amino acid sequence of (a) or (b):

(a) an amino acid sequence having at least 90% identity to the amino acid sequence of amino acid numbers 1006 to 1028 of SEQ ID NO: 2; or (b) the amino acid sequence of amino acid numbers 1006 to 1028 of SEQ ID NO: 2, or an amino acid sequence in which 1 to 2 amino acids are deleted, substituted, inserted and/or added in the amino acid sequence of amino acid numbers 1006 to 1028 of SEQ ID NO: 2.

In one embodiment, the transmembrane domain used in the present invention consists of the amino acid sequence of amino acid numbers 1006 to 1028 of SEQ ID NO: 2.

The structure of the endosomal/lysosomal targeting domain of LAMP is well known to those skilled in the art (WO 1994/017192). The endosomal/lysosomal targeting domain of LAMP has a function of transporting a protein to lysosome. As the endosomal/lysosomal targeting domain of LAMP used in the present invention, any suitable endosomal/lysosomal targeting domain of LAMP can be selected as long as it has a function of transporting the protein to lysosome. In one embodiment, endosomal/lysosomal targeting domain of LAMP used in the present invention is an endosomal/lysosomal targeting domain of LAMP-1.

In one embodiment, the endosomal/lysosomal targeting domain of LAMP used in the present invention consists of the amino acid sequence of amino acid numbers 1037 to 1040 of SEQ ID NO: 2, or an amino acid sequence in which 1 amino acid is deleted, substituted, inserted and/or added in the amino acid sequence of amino acid numbers 1037 to 1040 of SEQ ID NO: 2.

In one embodiment, the endosomal/lysosomal targeting domain of LAMP used in the present invention consists of an amino acid sequence in a range of amino acid numbers 1037 to 1040 of SEQ ID NO: 2.

In the chimeric protein relating to the present invention, the signal peptide, the intra-organelle stabilizing domain of LAMP, each allergen comprised in the allergen domain, the transmembrane domain, and the endosomal/lysosomal targeting domain of LAMP may be directly linked or may be indirectly linked via a linker peptide. The linker peptide to be used can be appropriately selected by those skilled in the art. In one embodiment, the linker peptide consists of 10 or less amino acids. In one embodiment, a linker peptide used between the intra-organelle stabilizing domain of LAMP and the allergen domain, between allergens, and between the allergen domain and the transmembrane domain is a linker peptide selected from the group consisting of LeuGlu, GlyGlyGlyGly, and GluPheThr. In one embodiment, the linker peptide used between the transmembrane domain and the endosomal/lysosomal targeting domain of LAMP is a linker peptide consisting of the amino acid sequence of amino acid numbers 1029 to 1036 of SEQ ID NO: 2.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide of LAMP, a nucleotide sequence encoding an intra-organelle stabilizing domain of LAMP, a nucleotide sequence encoding an allergen domain comprising Der p 1, Der p 2, Der p 23, and Der p 7, a nucleotide sequence encoding a transmembrane domain of LAMP, and a nucleotide sequence encoding an endosomal/lysosomal targeting domain of LAMP.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide of LAMP-1, a nucleotide sequence encoding the intra-organelle stabilizing domain of LAMP-1, a nucleotide sequence encoding an allergen domain comprising Der p 1, Der p 2, Der p 23, and Der p 7, a nucleotide sequence encoding a transmembrane domain of LAMP-1, and a nucleotide sequence encoding an endosomal/lysosomal targeting domain the of LAMP-1.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, a nucleotide sequence encoding a peptide linker consisting of the amino acid sequence of amino acid numbers 1029 to 1036 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide, a nucleotide sequence encoding an intra-organelle stabilizing domain of LAMP, a nucleotide sequence encoding an allergen domain comprising Der p 1, Der p 2, Der p 23, and Der p 7 in this order, a nucleotide sequence encoding a transmembrane domain, and a nucleotide sequence encoding an endosomal/lysosomal targeting domain of LAMP.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide of LAMP, a nucleotide sequence encoding an intra-organelle stabilizing domain of LAMP, a nucleotide sequence encoding an allergen domain comprising Der p 1, Der p 2, Der p 23, and Der p 7 in this order, a nucleotide sequence encoding a transmembrane domain of LAMP, and a nucleotide sequence encoding an endosomal/lysosomal targeting domain of LAMP.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide of LAMP-1, a nucleotide sequence encoding the intra-organelle stabilizing domain of LAMP-1, a nucleotide sequence encoding an allergen domain comprising Der p 1, Der p 2, Der p 23, and Der p 7 in this order, a nucleotide sequence encoding a transmembrane domain of LAMP-1, and a nucleotide sequence encoding an endosomal/lysosomal targeting domain of LAMP-1.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the nucleic acid of the present invention is the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, a nucleotide sequence encoding a peptide linker consisting of the amino acid sequence of amino acid numbers 1029 to 1036 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

The nucleic acid of the present invention is not particularly limited as long as it encodes the chimeric protein relating to the present invention, and has an action of inducing Th1-type immunity with respect to the allergen selected from the group consisting of Der p 1, Der p 2, Der p 23, and Der p 7, when the nucleic acid is administered to a human or an animal. One can confirm whether or not a certain nucleic acid has an action of inducing Th1-type immunity, when the nucleic acid is administered to a human or an animal, by the method described in, for example, Example 3 and/or Example 4. In addition, the nucleic acid of the present invention may be a nucleic acid having an action of inducing Th1 cell dominant immune response, when the nucleic acid is administered to a human or an animal. One can confirm whether or not a certain nucleic acid has an action of inducing Th1 cell dominant immune response, when the nucleic acid is administered to human or animal, by the method described in, for example, Example 4.

In one embodiment, the nucleic acid of the present invention is the following nucleic acid:

a nucleic acid comprising a nucleotide sequence encoding a chimeric protein consisting of an amino acid sequence having at least 90%, 92%, 94%, 96%, 98%, or 99% identity to the amino acid sequence shown by SEQ ID NO: 2.

In one embodiment, the nucleic acid of the present invention is the following nucleic acid:

a nucleic acid comprising a nucleotide sequence encoding a chimeric protein consisting of an amino acid sequence having at least 90% identity to the amino acid sequence shown by SEQ ID NO: 2.

In one embodiment, the nucleic acid of the present invention is the following nucleic acid:

a nucleic acid comprising a nucleotide sequence encoding a chimeric protein consisting of the amino acid sequence shown by SEQ ID NO: 2, or a chimeric protein consisting of an amino acid sequence in which 1 to 10 amino acids are deleted, substituted, inserted and/or added in the amino acid sequence shown by SEQ ID NO: 2.

In one embodiment, the nucleic acid of the present invention is the following nucleic acid:

a nucleic acid comprising a nucleotide sequence encoding a chimeric protein consisting of an amino acid sequence having at least 90% identity to the amino acid sequence shown by SEQ ID NO: 2, wherein the nucleic acid has an action of inducing Th1-type immunity to the allergen selected from the group consisting of Der p 1, Der p 2, Der p 23, and Der p 7.

In one embodiment, the nucleic acid of the present invention is the following nucleic acid:

a) a nucleic acid comprising a nucleotide sequence encoding a chimeric protein consisting of the amino acid sequence shown by SEQ ID NO: 2 or b) a nucleic acid comprising a nucleotide sequence encoding a chimeric protein consisting of an amino acid sequence in which 1 to 10 amino acids are deleted, substituted, inserted and/or added in the amino acid sequence shown by SEQ ID NO: 2, wherein the nucleic acid has an action of inducing Th1-type immunity to an allergen selected from the group consisting of Der p 1, Der p 2, Der p 23, and Der p 7.

In one embodiment, the nucleic acid of the present invention is the following nucleic acid:

a nucleic acid comprising a nucleotide sequence encoding a chimeric protein consisting of an amino acid sequence having at least 90% identity to the amino acid sequence shown by SEQ ID NO: 2, wherein the nucleic acid has an action of inducing Th1-type immunity to Der p 1, Der p 2, Der p 23, and Der p 7.

In one embodiment, the nucleic acid of the present invention is the following nucleic acid:

a) a nucleic acid comprising a nucleotide sequence encoding a chimeric protein consisting of the amino acid sequence shown by SEQ ID NO: 2 or b) a nucleic acid comprising a nucleotide sequence encoding a chimeric protein consisting of an amino acid sequence in which 1 to 10 amino acids are deleted, substituted, inserted and/or added in the amino acid sequence shown by SEQ ID NO: 2, wherein the nucleic acid has an action of inducing Th1-type immunity to Der p 1, Der p 2, Der p 23, and Der p 7.

In one embodiment, the nucleic acid of the present invention is the following nucleic acids a nucleic acid comprising a nucleotide sequence encoding a chimeric protein consisting of the amino acid sequence shown by SEQ ID NO: 2.

In one embodiment, the nucleotide sequence encoding the chimeric protein consisting of the amino acid sequence shown by SEQ ID NO: 2 means the nucleotide sequence shown by SEQ ID NO: 1.

Based on the nucleotide sequence, the nucleic acid of the present invention can be easily prepared by those skilled in the art by using methods known in the art. For example, the nucleic acid of the present invention can be synthesized by using gene synthesis methods known in the art. As such a gene synthesis method, various methods known to those skilled in the art such as a method for synthesizing an antibody gene described in WO 90/07861 can be used.

Once being synthesized, the nucleic acid of the present invention can be easily replicated by those skilled in the art using methods known in the art. For example, the nucleic acid of the present invention can be replicated by the method described later in
<Method for Producing the Nucleic Acid of the Present Invention and Nucleic Acid Which can be Produced by the Method>.

<Expression Vector of the Present Invention>

The expression vector of the present invention includes an expression vector comprising the nucleic acid of the present invention.

The expression vector used to express a chimeric protein from the nucleic acid of the present invention is not particularly limited as long as it can express the chimeric protein from the nucleic acid of the present invention in the animal cells. In one embodiment, the expression vector used to express a chimeric protein from the nucleic acid of the present invention is an expression vector which can be used for expressing the chimeric protein in a human body. Examples of the expression vector used in the present invention include a plasmid vector, a viral vector (for example, adenovirus, retrovirus, adeno-associated virus) and the like. In one embodiment, the expression vector of the present invention is a plasmid vector. In the present specification, “plasmid” means the plasmid vector.

The expression vector of the present invention may comprise a promoter operably linked to the nucleic acid of the present invention. Examples of the promoter for expressing the chimeric protein from the nucleic acid of the present invention in animal cells include a virus-derived promoter such as CMV (cytomegalovirus), RSV (respiratory syncytial virus), and SV40 (simian virus 40), an actin promoter, EF (elongation factor) 1α promoter, a heat shock promoter and the like. In one embodiment, the promoter comprised in the expression vector of the present invention is a CMV promoter. The expression vector of the present invention may comprise a start codon and a stop codon. In this case, an enhancer sequence, an untranslated region, a splicing junction, a polyadenylation site, or a replicable unit may be comprised.

In one embodiment, the expression vector of the present invention is an expression vector comprising the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the expression vector of the present invention is an expression vector comprising the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, a nucleotide sequence encoding a peptide linker consisting of the amino acid sequence of amino acid numbers 1029 to 1036 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the expression vector of the present invention is an expression vector comprising the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the expression vector of the present invention is an expression vector comprising the following nucleic acid:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, a nucleotide sequence encoding a peptide linker consisting of the amino acid sequence of amino acid numbers 1029 to 1036 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the expression vector of the present invention is an expression vector comprising a nucleic acid comprising a nucleotide sequence encoding a chimeric protein consisting of the amino acid sequence shown by SEQ ID NO: 2.

In one embodiment, the expression vector of the present invention is an expression vector comprising a nucleic acid comprising the nucleotide sequence shown by SEQ ID NO: 1.

In one embodiment, the expression vector of the present invention is an expression vector comprising a nucleic acid consisting of the nucleotide sequence shown by SEQ ID NO: 3.

<Host Cell of the Present Invention>

The host cell of the present invention includes a host cell transformed with the nucleic acid of the present invention. In one embodiment, the host cell of the present invention is a host cell transformed with the expression vector of the present invention. In one embodiment, the host cell of the present invention is a host cell transformed with the expression vector of the present invention which is a plasmid vector.

The host cell transformed with the nucleic acid of the present invention is not particularly limited, and any cell known in the art can be selected as long as it is a cell that can be used for nucleic acid replication.

Examples of the host cell that can be used for nucleic acid replication include various cells such as natural cells or artificially established cells commonly used in the technical field of the present invention (for example, animal cells (for example, CHOK1SV cells), insect cells (for example, Sf9), bacteria (for example, *E. coli*), and yeasts (for example, *Saccharomyces* and *Pichia*)). In one embodiment, *E. coli* can be used as a host cell. Transformation itself can be carried out by known methods.

<Method for Producing the Nucleic Acid of the Present Invention and Nucleic Acid Which can be Produced by the Method>

Examples of the method for producing the nucleic acid of the present invention include a method for producing a nucleic acid or an expression vector, which comprises a step of culturing host cells transformed with the nucleic acid or the expression vector of the present invention. In one embodiment, the method for producing the nucleic acid of the present invention comprises a step of culturing the host cell transformed with the nucleic acid of the present invention, and replicating the nucleic acid of the present invention. In one embodiment, the method for producing the nucleic acid of the present invention comprises a step of culturing the host cell transformed with the expression vector of the present invention, and replicating the expression vector of the present invention.

In one embodiment, the host cell used in the method for producing the nucleic acid of the present invention is *E. coli*. For culture of *E. coli*, an appropriate culture medium such as LB medium, M9 medium, Terrific Broth medium, SOB medium, SOC medium, or 2× YT medium can be selected.

In addition, the culturing of *E. coli* can be carried out in an environment where carbon (it is not particularly limited as long as it is an assimilable carbon compound; for example, polyols such as glycerin, or organic acids such as pyruvic acid, succinic acid, or citric acid), nitrogen (it is not particularly limited as long as it is a nitrogen compound that can be used by *E. coli*; for example, peptone, meat extract, yeast extract, casein hydrolysate, soybean meal alkaline extract, or ammonia or a salt thereof), inorganics and inorganic ions (it is not particularly limited, and examples thereof include phosphate, carbonate, sulfate, magnesium, calcium, potassium, iron, manganese and zinc), a vitamin source, and an antifoaming agent are controlled to an appropriate concentration. In addition, the control of culturing includes control of parameters such as pH, temperature, stir, air flow and dissolved oxygen. In one embodiment, the conditions of culturing include pH of 6.7 to 7.5, temperature of 20° C. to 37° C., and a stirring speed of 200 to 300 rpm.

The method for producing the nucleic acid of the present invention may comprise a step of obtaining lysate from collected culture solutions. The lysate can be obtained, for example, by treating the collected culture solutions with an alkaline lysis method or boiling method. Also, the step of obtaining the lysate may include a step of sterile filtration of a final lysate material.

The method for producing the nucleic acid of the present invention may further comprise a step of purifying nucleic acid or an expression vector from lysate. Ion exchange chromatography and/or hydrophobic interaction chromatography can be used to purify the nucleic acid or the expression vector from the lysate. The step of purifying the nucleic acid or the expression vector from the lysate may include a step of ultrafiltration and/or diafiltration. In addition, as a final treatment of the purification step, a sterile filtration step may be comprised.

In one embodiment, the nucleic acid of the present invention is a nucleic acid produced by the method for producing the nucleic acid of the present invention.

In one embodiment, the expression vector of the present invention is an expression vector produced by the method for producing the nucleic acid of the present invention.

<Pharmaceutical Composition of the Present Invention>

The pharmaceutical composition of the present invention includes a pharmaceutical composition comprising the nucleic acid of the present invention and a pharmaceutically acceptable excipient. In one embodiment, the pharmaceutical composition of the present invention is a pharmaceutical composition comprising the vector of the present invention and the pharmaceutically acceptable excipient. The pharmaceutical composition of the present invention can be prepared by a generally used method with an excipient generally used in the field, that is, a pharmaceutical excipient, a pharmaceutical carrier or the like. Examples of dosage forms of these pharmaceutical compositions include, for example, parenteral agents such as injections and drip agents, which can be administered by intravenous administration, subcutaneous administration, intradermal administration, and intramuscular administration. In formulating, excipients, carriers, additives, and the like can be used according to these dosage forms within the pharmaceutically acceptable range.

In one embodiment, the pharmaceutical composition of the present invention is a pharmaceutical composition comprising the nucleic acid or the expression vector of the present invention and the pharmaceutically acceptable excipient.

While the administration amount of the nucleic acid of the present invention or the expression vector varies depending on the degree of symptoms and age of the patient, and the dosage form of the preparation used, for example, the amount in a range of 0.001 mg/kg to 100 mg/kg can be used. Further, it is possible to prepare a formulation by adding the nucleic acid or the expression vector of the present invention in an amount corresponding to such administration amount.

The pharmaceutical composition of the present invention can be used as an agent for preventing or treating allergy caused by an allergen selected from Der p 1, Der p 2, Der p 23, and Der p 7. Further, the pharmaceutical composition of the present invention can be used as an agent for prevention or treating the mite allergy.

The present invention includes a pharmaceutical composition for preventing or treating allergy, comprising the nucleic acid of the present invention. In addition, the present invention includes a method for preventing or treating allergy, comprising administering a prophylactically effective or therapeutically effective amount of the nucleic acid of the present invention. The present invention also includes the nucleic acid of the present invention for use in preventing or treating allergy. In addition, the present invention includes use of the nucleic acid of the present invention for the manufacture of a pharmaceutical composition for preventing or treating allergy. In one embodiment, the above-described allergy is allergy caused by an allergen selected from the group consisting of Der p 1, Der p 2, Der p 23, and Der p 7. In addition, in one embodiment, the above-described allergy is allergy affecting an allergy patient having an antibody that responds to an allergen selected from the group consisting of Der p 1, Der p 2, Der p 23, and Der p 7. Further, in one embodiment, the above-described allergy is mite allergy.

In one embodiment, the pharmaceutical composition of the present invention is a pharmaceutical composition for preventing or treating allergy, comprising the following nucleic acid and a pharmaceutically acceptable excipient:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the pharmaceutical composition of the present invention is a pharmaceutical composition for preventing or treating allergy, comprising the following nucleic acid and a pharmaceutically acceptable excipient:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the pharmaceutical composition of the present invention is a pharmaceutical composition for preventing or treating allergy, comprising a nucleic acid comprising a nucleotide sequence encoding a chimeric protein consisting of the amino acid sequence shown by SEQ ID NO: 2 and a pharmaceutically acceptable excipient.

The present invention includes a pharmaceutical composition for preventing or treating allergy, comprising the expression vector of the present invention. In addition, the present invention includes a method for preventing or treating allergy, comprising administering a prophylactically effective or therapeutically effective amount of the expression vector of the present invention. The present invention also includes the expression vector of the present invention for use in preventing or treating allergy. In addition, the present invention includes use of the expression vector of the present invention for the manufacture of a pharmaceutical composition for preventing or treating allergy. In one embodiment, the above-described allergy is allergy caused by an allergen selected from the group consisting of Der p 1, Der p 2, Der p 23, and Der p 7. In addition, in one embodiment, the above-described allergy is allergy affecting an allergy patient having an antibody that responds to an allergen selected from the group consisting of Der p 1, Der p 2, Der p 23, and Der p 7. Further, in one embodiment, the above-described allergy is mite allergy.

In one embodiment, the pharmaceutical composition of the present invention is a pharmaceutical composition for preventing or treating allergy, comprising an expression vector comprising the following nucleic acid and a pharmaceutically acceptable excipient:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the pharmaceutical composition of the present invention is a pharmaceutical composition for preventing or treating allergy, comprising an expression vector comprising the following nucleic acid and a pharmaceutically acceptable excipient:

a nucleic acid comprising a nucleotide sequence encoding a chimeric protein, wherein the nucleotide sequence is a nucleotide sequence comprising the following nucleotide sequences in this order:

a nucleotide sequence encoding a signal peptide consisting of the amino acid sequence of amino acid numbers 1 to 27 of SEQ ID NO: 2, a nucleotide sequence encoding an intra-organelle stabilizing domain of LAMP consisting of the amino acid sequence of amino acid numbers 28 to 380 of SEQ ID NO: 2, a nucleotide sequence encoding an allergen domain comprising Der p 1 consisting of the amino acid sequence of amino acid numbers 383 to 594 of SEQ ID NO: 2, Der p 2 consisting of the amino acid sequence of amino acid numbers 599 to 727 of SEQ ID NO: 2, Der p 23 consisting of the amino acid sequence of amino acid numbers 732 to 800 of SEQ ID NO: 2, and Der p 7 consisting of the amino acid sequence of amino acid numbers 805 to 1002 of SEQ ID NO: 2 in this order, a nucleotide sequence encoding a transmembrane domain consisting of the amino acid sequence of amino acid numbers 1006 to 1028 of SEQ ID NO: 2, and a nucleotide sequence encoding an endosomal/lysosomal targeting domain of LAMP consisting of the amino acid sequence of amino acid numbers 1037 to 1040 of SEQ ID NO: 2.

In one embodiment, the pharmaceutical composition of the present invention is a pharmaceutical composition for preventing or treating allergy, comprising an expression vector comprising a nucleic acid comprising a nucleotide sequence encoding a chimeric protein consisting of the amino acid sequence shown by SEQ ID NO: 2 and a pharmaceutically acceptable excipient.

Specific examples are provided herein for reference in order to obtain further understanding of the present invention; however, these examples are for the purpose of illustration and the present invention is not limited thereto.

EXAMPLES

Example 1

Construction of LAMP-Der p 1-Der p 2-Der p 23-Der p 7 Plasmid

LAMP-Der p 1-Der p 2-Der p 23-Der p 7 plasmid consisting of the nucleotide sequence shown by SEQ ID NO: 3 (an expression vector comprising a nucleic acid comprising a nucleotide sequence comprising the following nucleotide sequences in this order (that is, a nucleotide sequence encoding a chimeric protein consisting of the amino acid sequence shown by SEQ ID NO: 2): a nucleotide sequence encoding a signal peptide of LAMP-1 (the amino acid sequence of 1 to 27 of SEQ ID NO: 2), a nucleotide sequence encoding an intra-organelle stabilizing domain of LAMP-1 (the amino acid sequence of 28 to 380 of SEQ ID NO: 2), a nucleotide sequence encoding an allergen domain comprising Der p 1, Der p 2, Der p 23, and Der p 7 in this order (the amino acid sequence of 383 to 1002 of SEQ ID NO: 2), a nucleotide sequence encoding a transmembrane domain of LAMP-1 (the amino acid sequence of 1006 to 1028 of SEQ ID NO: 2), and a nucleotide sequence encoding an endosomal/lysosomal targeting domain of LAMP-1 (the amino acid sequence of 1037 to 1040 of SEQ ID NO: 2)) was constructed. The plasmid can be constructed by inserting synthetic DNA, in which Xho I recognition sequence is added to 5' end of the nucleotide sequence of 1147 to 3006 of SEQ ID NO: 1 (a nucleotide sequence encoding an allergen domain comprising Der p 1, Der p 2, Der p 23, and Der p 7 in this order) and Eco RI recognition sequence is added to the 3' end of the nucleic acid sequence, into Eco RI-Xho I site of the plasmid shown by SEQ ID NO: 6 of Japanese Patent No. 5807994. *E. coli* was transformed with the constructed LAMP-Der p 1-Der p 2-Der p 23-Der p 7 plasmid and cultured in a liquid medium. The amplified LAMP-Der p 1-Der p 2-Der p 23-Der p 7 plasmid was obtained by a method of centrifuging the culture solution and collecting the cells based on a general plasmid extraction and purification method (miniprep method).

Example 2

Expression of LAMP-Der p 1-Der p 2-Der p 23-Der p 7 Chimeric Protein

In vitro expression of the LAMP-Der p 1-Der p 2-Der p 23-Der p 7 chimeric protein (a chimeric protein consisting of an amino acid sequence encoded by the nucleotide sequence shown by SEQ ID NO: 1 (that is, the amino acid sequence shown by SEQ ID NO: 2)) by using human fetal kidney-derived 293T cell line was evaluated.

(1) Cell Culture and Plasmid Introduction

Human fetal kidney-derived 293T cells (Thermo Fisher Scientific, Cat. HCL4517) were seeded in 6-well plates (Cat. 3810-006 manufactured by IWAKI) at $3\times10^5$ cells/well in D-MEM medium (Sigma-Aldrich, Cat. D5796) containing 10% fetal bovine serum (Hyclone, Cat. SH30070.03) and 100-fold diluted penicillin-streptomycin (Thermo Fisher Scientific, Cat. 15070063). After overnight culture of the seeded cells at 37° C. in the presence of 5% $CO_2$, a mixed solution having a ratio of LAMP-Der p 1-Der p 2-Der p 23-Der p 7 plasmid: Lipofectamine 2000 (Thermo Fisher Scientific, Cat. 11668027)=2.5 (μg): 10 (μL) was added. After overnight culture of the seeded cells at 37° C. in the presence of 5% $CO_2$ again, the medium was removed and washed once with PBS, and then western blotting was performed.

(2) Western Blotting

Pretreatment: Cells were lysed in RIPA buffer (Pierce, Cat. 89900) containing a protease inhibitor (Sigma-Aldrich, Cat. 1873580), and the protein concentration of the supernatant after centrifugation at 20,000×g for 5 minutes was measured. To 5 μL of the cell lysate diluted with PBS containing protease inhibitor, 5 μL of LDS sample buffer (Thermo Fisher Scientific, Cat. NP0007) containing 100 mM DTT was added so that the protein concentration would be 200 μg/mL, and heat-treated at 70° C. for 10 minutes.

SDS-PAGE: Using NuPAGE (Registered trademark) MOPS SDS Running buffer (Thermo Fisher Scientific, Cat. NP0001) and NuPAGE (Registered trademark) 4%-12% Bis-Tris Gel (Thermo Fisher Scientific, Cat. NP0323), the above-mentioned pretreated cell lysate was applied to the gel and electrophoresis was performed at a constant voltage of 200 V.

Blotting: Blotting was performed by bringing PVDF membrane (Thermo Fisher Scientific, Cat. LC2005) into contact with the gel after SDS-PAGE, and electrifying for 90 minutes at 180 mA in XCell II Blot Module (Thermo Fisher Scientific, Cat. EI9051) filled with NuPAGE (Registered trademark) Transfer buffer (Thermo Fisher Scientific, Cat. NP0006) containing 20% of methanol.

Blocking: The membrane after electrification was immersed in Blocking One (Nacalai Tesque, Cat. 03953-95) and shaken at room temperature for one hour.

Primary antibody: Anti-human LAMP-1 antibody (Sino biological, Cat. 11215-RP01) was added at 1000-fold dilution in TBS Tween-20 buffer (Thermo Fisher Scientific, Cat. 28360) containing 10% of Blocking One. The membrane was immersed in this buffer and shaken overnight at 4° C.

Secondary antibody: The membrane was washed with TBS Tween-20 buffer. Anti-rabbit IgG (H+L chain) pAb-HRP (MBL, Cat. 458) was added at 3000-fold dilution in TBS Tween-20 buffer containing 10% of Blocking One. The membrane was immersed in this buffer and shaken at room temperature for one hour.

Detection: The membrane was washed with TBS Tween-20 buffer. The membrane was immersed in ECL prime western blotting detection reagent (GE Healthcare, Cat. RPN2232), and an image was detected with LumiVision PRO 400EX (Aisin Seiki Co., Ltd.). In the image, a band responsive to the anti-human LAMP-1 antibody corresponding to the chimeric protein was detected.

As the result of the above-mentioned tests, it was confirmed that LAMP-Der p 1-Der p 2-Der p 23-Der p 7 chimeric protein in the cell was expressed by introducing the LAMP-Der p 1-Der p 2-Der p 23-Der p 7 plasmid to the human fetal kidney-derived 293T cell line.

Example 3

Induction of IgG2a Production by Administration of LAMP-Der p 1-Der p 2-Der p 23-Der p 7 Plasmid Evaluation of induction of antibody production in vivo was performed. In eight examples in each group, 25 μL of a PBS solution containing 50 μg of LAMP-Der p 1-Der p 2-Der p 23-Der p 7 plasmid was administered in the ear of 7-week-old BALB/c female mice (Charles River Laboratories Japan, Inc.) at the start of administration intradermally three times every week (Day 0, 7 and 14). One week after the final administration, blood was collected and plasma samples were obtained (Day 21). As a control, LAMP-Der p 23-Der p 7-Der p 2-Der p 1 plasmid (an expression vector comprising a nucleic acid comprising a nucleotide sequence comprising the following nucleotide sequences in this order: a nucleotide sequence encoding the amino acid sequence of amino acid numbers 1 to 380 of SEQ ID NO: 2 (hereinafter, refer to as N-terminal of LAMP-1 in Examples 3 and 4), a nucleotide sequence encoding an allergen domain comprising Der p 23 consisting of the amino acid sequence of amino acid numbers 732 to 800 of SEQ ID NO: 2 (hereinafter, refer to as Der p 23 domain in Examples 3 and 4), Der p 7 consisting of the amino acid sequence of amino acid numbers 805 to 1002 of SEQ ID NO: 2 (hereinafter, refer to as Der p 7 domain in Examples 3 and 4), Der p 2 consisting of the amino acid sequence of amino acid numbers 599 to 727 of SEQ ID NO: 2 (hereinafter, refer to as Der p 2 domain in Examples 3 and 4), and Der p 1 consisting of the amino acid sequence of amino acid numbers 383 to 594 of SEQ ID NO: 2 (hereinafter, refer to as Der p 1 domain in Examples 3 and 4) in this order, and a nucleotide sequence encoding the amino acid sequence of amino acid numbers 1006 to 1040 of SEQ ID NO: 2 (hereinafter, refer to as C-terminal of LAMP-1 in Examples 3 and 4)); a mixture of LAMP-Der p 1-Der p 2 plasmid (an expression vector comprising a nucleic acid comprising a nucleotide sequence comprising the following nucleotide sequences in this order: a nucleotide sequence encoding N-terminal of LAMP-1, a nucleotide sequence encoding an allergen domain comprising Der p 1 domain and Der p 2 domain in this order, and a nucleotide sequence encoding C-terminal of LAMP-1) and LAMP-Der p 23-Der p 7 plasmid (an expression vector comprising a nucleic acid comprising a nucleotide sequence comprising the following nucleotide sequences in this order: a nucleotide sequence encoding N-terminal of LAMP-1, a nucleotide sequence encoding allergen domain containing Der p 23 domain and Der p 7 domain in this order, and a nucleotide sequence encoding C-terminal of LAMP-1); and a mixture of LAMP-Der p 1 plasmid (an expression vector comprising a nucleic acid comprising a nucleotide sequences comprising the following nucleotide sequences in this order: a nucleotide sequence encoding N-terminal of LAMP-1, a nucleotide sequence encoding an allergen domain comprising Der p 1 domain, and a nucleotide sequence encoding C-terminal of LAMP-1), LAMP-Der p 2 plasmid (an expression vector comprising a nucleic acid comprising a nucleotide sequence comprising the following nucleotide sequences in this order: a nucleotide sequence encoding N-terminal of LAMP-1, a nucleotide sequence encoding an allergen domain comprising Der p 2 domain, and a nucleotide sequence encoding C-terminal of LAMP-1), LAMP-Der p 7 plasmid (an expression vector comprising a nucleic acid comprising a nucleotide sequence comprising the following nucleotide sequences in this order: a nucleotide sequence encoding N-terminal of LAMP-1, a nucleotide sequence encoding an allergen domain comprising Der p 7 domain, and a nucleotide sequence encoding C-terminal of LAMP-1), and LAMP-Der p 23 plasmid (an expression vector comprising a nucleic acid comprising a nucleotide sequence comprising the following nucleotide sequences in this order: a nucleotide sequence encoding N-terminal of LAMP-1, a nucleotide sequence encoding an allergen domain comprising Der p 23 domain, and a nucleotide sequence encoding C-terminal of LAMP-1) were prepared. Each control plasmid can be prepared by the same method as the method described in Example 1. To mice, 25 μL of PBS solution containing 50 μg of the above plasmid or the above plasmid mixture or 25 μL of PBS was administered. An antibody titer was measured by ELISA using a 100-fold or 1000-fold diluted plasma sample, and the absorbance at 450 nm was measured. ELISA measurement was performed based on a general ELISA method using F96 MAXISORP NUNC-IMMUNO PLATE (Nunc, Cat. 439454) as a test plate. Der p 1 which is a purified protein (Indoor biotechnologies, NA-DP1-1, lot: 38052), Der p 2 which is a purified protein (Indoor biotechnologies, NA-DP2-1, lot: 36118), Der p 7 which is a recombinant purified protein (Indoor biotechnologies, RP-DP7-1, lot: 34033), or Der p 23 which is a recombinant purified protein (Sysmex, UniProtKB: A0A0K2DQU8) is prepared to 1 μg/mL with PBS, added at 50 μL/well and allowed to stand overnight at 4° C. After washing a test plate three times with a washing buffer (PBS Tween-20 buffer; Thermo Fisher Scientific, Cat. 28352), 100 μL/well of PBS containing 1% of BSA (Sigma-Aldrich, Cat. A8022) was added and allowed to stand at room temperature for one hour. After washing three times with the washing buffer, 50 μL/well of a 100-fold or 1000-fold diluted plasma sample in PBS containing 1% of BSA was added and allowed to stand at room temperature for one hour. After washing three times with the washing buffer, 50 μL/well of a 50000-fold diluted secondary antibody, Goat anti-mouse IgG2a HRP Conjugated (Bethyl Laboratories, Cat. A90-107P), in PBS containing 1% of BSA was added, and the test plate was allowed to stand at room temperature for one hour. After washing three times with the washing buffer, 50 μL/well of TMB Microwell Peroxidase Substrate System (SeraCare Life Sciences, Inc., Cat.50-76-03) which is a substrate solution was added and the plate was allowed to stand at room temperature for 15 minutes with blocking light. A reaction stop solution (2N $H_2SO_4$) was added at 50 μL/well and absorbance at 450 nm was measured.

As the result of the above-mentioned tests, the production of Der p 1, Der p 2, Der p 23 and Der p 7 specific IgG2a was detected by administering LAMP-Der p 1-Der p 2-Der p 23-Der p 7 plasmid (Der p1-p2-p23-p7) to mice (FIG. 1). On the other hand, even when LAMP-Der p 23-Der p 7-Der p 2-Der p 1 plasmid (Der p23-p7-p2-p1), a mixture of LAMP-Der p 1-Der p 2 plasmid and LAMP-Der p 23-Der p 7 plasmid (Der p1-p2+Der p23-p7), and a mixture of LAMP-Der p 1 plasmid, LAMP-Der p 2 plasmid, LAMP-Der p 7 plasmid and LAMP-Der p 23 plasmid (4 plasmid mix) were administered to the mice, the production of Der p 1-specific IgG2a was not detected. In addition, when a mixture of LAMP-Der p 1-Der p 2 plasmid and LAMP-Der p 23-Der p 7 plasmid (Der p1-p2+Der p23-p7) is administered to mice, the production of Der p 2 specific IgG 2a was not detected as well. That is, it was only the LAMP-Der p 1-Der p 2-Der p 23-Der p 7 plasmid that the production of IgG2a specific for all allergens encoded in the plasmid was detected. From the above results, it has been suggested that among the tested plasmids, only LAMP-Der p 1-Der p 2-Der p 23-Der p 7 plasmid induces Th1 immune responses for all the allergens and causes class switch of activated B cells to the IgG2a isotype.

Example 4

Figure 2:
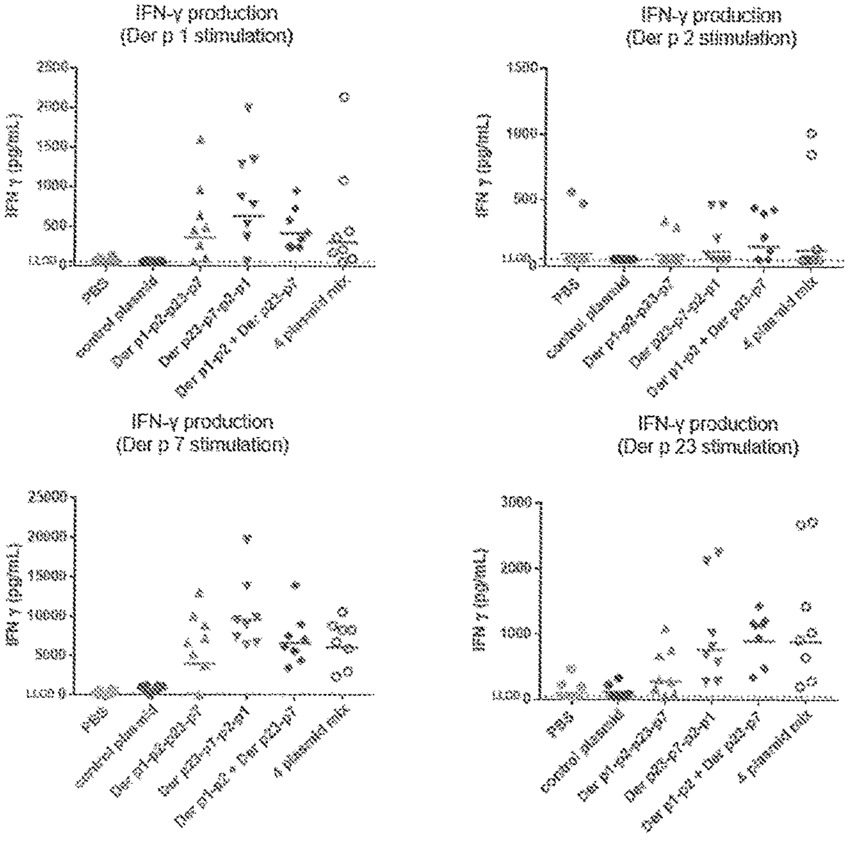
FIG. 2 illustrates IFN-γ production when spleen cells of mice to which the nucleic acid of the present invention has been administered were stimulated with Der p 1 protein, Der p 2 protein, Der p 7 protein, or Der p 23 protein. The vertical axis indicates the concentration of IFN-γ in the culture supernatant (pg/mL), and the horizontal axis indicates each administration group. The horizontal lines indicate arithmetic mean values. The dotted line indicates the value of lower limit of detection (LLOD).
Figure 3:
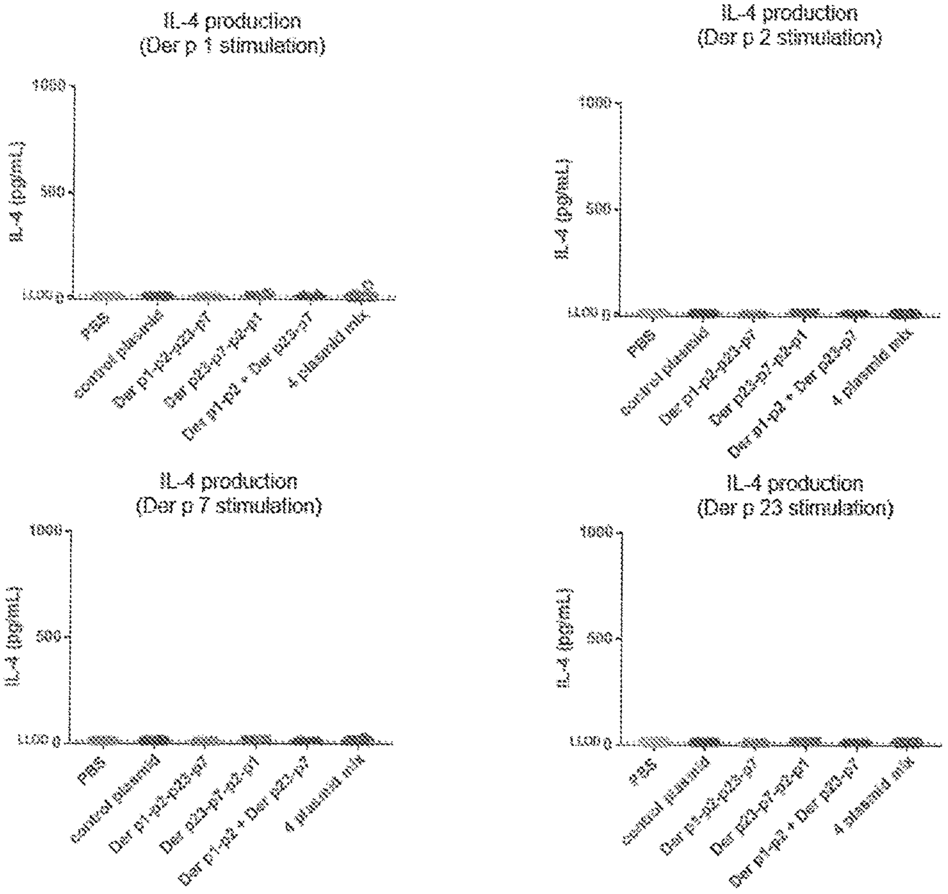
FIG. 3 illustrates IL-4 production when spleen cells of mice to which the nucleic acid of the present invention has been administered were stimulated with Der p 1 protein, Der p 2 protein, Der p 7 protein, or Der p 23 protein. The vertical axis indicates the concentration of IL-4 in the culture supernatant (pg/mL), and the horizontal axis indicates each administration group. The horizontal lines indicate arithmetic mean values. The dotted line indicates the value of lower limit of detection (LLOD).

Induction of IFN-γ and IL-4 Production by LAMP-Der p 1-Der p 2-Der p 23-Der p 7 Plasmid Evaluation of cytokine production induction upon stimulation with allergen was performed on splenocytes collected from mice administered with LAMP-Der p 1-Der p 2-Der p 23-Der p 7 plasmid. Splenocytes were prepared according to a general method from the mice used in Example 3 and the mice administered with a control plasmid (an expression vector comprising a nucleic acid comprising a nucleotide sequence comprising the following nucleotide sequences in this order: a nucleotide sequence encoding N-terminal of LAMP-1 and a nucleotide sequence encoding C-terminal of LAMP-1) with the same protocol as in Example 3 on Day 63. The control plasmid can be prepared by deleting Eco RI-Xho I site of the plasmid shown by SEQ ID NO: 6 of Japanese Patent No. 5807994. Splenocytes were seeded in 96-well plates (Cat. 3860-096 manufactured by IWAKI) at 8 x $10^5$ cells/well in RPMI-1640 medium (Sigma-Aldrich, Cat. R8758) containing 10% fetal bovine serum (Hyclone, Cat. SH30070.03) and 100-fold diluted penicillin-streptomycin (ThermoFisher Scientific, Cat. 15070063). Der p 1 (Indoor biotechnologies, NA-DP1-1, lot: 38052), Der p 2 (Indoor biotechnologies, NA-DP2-1, lot: 36118), Der p 7 (Indoor biotechnologies, RP-DP7-1, lot: 34033), or Der p 23 (Sysmex, UniProtKB: A0A0K2DQU8) were added such that the final concentrations thereof were respectively 3, 3, 3, and 1.3 μg/mL. Culturing was performed at 37° C. under 5% of $CO_2$ for 72 hours. The concentrations of IFN-γ and IL-4 in the culture supernatant were measured by ELISA method. A supernatant sample diluted 10-fold with TBS containing 0.1% BSA and 0.05% Tween 20 was used for the measurement of IFN-y, and a supernatant undiluted sample was used for the measurement of IL-4. As a test plate for ELISA measurement, F96 MAXISORP NUNC-IMMUNO PLATE (Nunc, Cat. 439454) was used. The measurement was carried out using mouse IFN-γ DuoSet ELISA (R&D Systems, Cat. DY485) and mouse IL-4 DuoSet ELISA (R&D Systems, Cat. DY 404) according to attached protocol. As the result of the above-mentioned test, a mite-derived allergen-specific IFN-γ production was induced by administering 50 μg of LAMP-Der p 1-Der p 2-Der p 23-Der p 7 plasmid (Der p 1-p2-p 23-p 7) to mice three times (FIG. 2). Also, even in a case where LAMP-Der p 23-Der p 7-Der p 2-Der p 1 plasmid (Der p23-p7-p2-p1), a mixture of LAMP-Der p 1-Der p 2 plasmid and LAMP-Der p 23-Der p 7 plasmid (Der p1-p2+Der p23-p7), and a mixture of LAMP-Der p 1 plasmid, LAMP-Der p 2 plasmid, LAMP-Der p 7 plasmid,and LAMP-Der p 23 plasmid (4 plasmid mix) were administered to the mice three times, comparable mite-derived allergen-specific IFN-γ production was induced. On the other hand, in the mice administered three times with 50 μg of LAMP-Der p 1-Der p 2-Der p 23-Der p 7 plasmid (Der p 1-p2-p23-p'7), the mite-derived allergen-specific IL-4 production was the lower limit of detection (FIG. 3). Even in a case where LAMP-Der p 23-Der p 7-Der p 2-Der p 1 plasmid (Der p23-p7-p2-p1), a mixture of LAMP-Der p 1-Der p 2 plasmid and LAMP-Der p 23-Der p 7 plasmid (Der p1-p2+Der p23-p'7), and a mixture of LAMP-Der p 1 plasmid, LAMP-Der p 2 plasmid, LAMP-Der p 7 plasmid, and LAMP-Der p 23 plasmid (4 plasmid mix) were administered to the mice three times, the mite-derived allergen-specific IL-4 production was below the lower limit of detection.

As the result of the above-mentioned tests, a mixture of LAMP-Der p 1-Der p 2-Der p 23-Der p 7 plasmid, LAMP-Der p 23-Der p 7-Der p 2-Der p 1 plasmid, LAMP-Der p 1-Der p 2 plasmid, and LAMP-Der p 23-Der p 7 plasmid, and a mixture of LAMP-Der p 1 plasmid, LAMP-Der p 2 plasmid, LAMP-Der p 7 plasmid, and LAMP-Der p 23 plasmid have been shown to induce Th1 cell dominant immune responses.

INDUSTRIAL APPLICABILITY

The nucleic acid of the present invention is expected to be useful for the prevention or treatment of mite allergy. In addition, the method for producing the nucleic acid of the present invention is useful for producing the nucleic acid.

Sequence Listing Free Text

The numerical heading <223> in the following sequence listing describes the description of "Artificial Sequence". Specifically, the nucleotide sequence shown by SEQ ID NO: 1 in the sequence listing is a nucleotide sequence encoding LAMP-Der p 1-Der p 2-Der p 23-Der p 7 chimeric protein, and the amino acid sequence shown by SEQ ID NO: 2 in the sequence listing is the amino acid sequence encoded by SEQ ID NO: 1. In addition, the nucleotide sequence shown by SEQ ID NO: 3 is the nucleotide sequence of LAMP-Der p 1-Der p 2-Der p 23-Der p 7 plasmid.

The invention claimed is:

1. A nucleic acid encoding a chimeric protein, wherein the nucleic acid comprises the following nucleotide sequences in this order:

a nucleotide sequence encoding a signal peptide;

a nucleotide sequence encoding an intra-organelle stabilizing domain of lysosome-associated membrane proteins (LAMP) consisting of amino acids 28 to 380 of SEQ ID NO: 2;

a nucleotide sequence encoding an allergen domain consisting of amino acids 383 to 1002 of SEQ ID NO: 2;

a nucleotide sequence encoding a transmembrane domain of LAMP-1 consisting of amino acids 1006 to 1028 of SEQ ID NO: 2; and a nucleotide sequence encoding an endosomal/lysosomal targeting domain of LAMP-1 consisting of amino acids 1037 to 1040 of SEQ ID NO: 2.

2. The nucleic acid according to claim 1, wherein the signal peptide is a signal peptide of LAMP.

3. The nucleic acid according to claim 1, wherein the signal peptide consists of amino acid numbers 1 to 27 of SEQ ID NO: 2.

4. An expression vector comprising:

the nucleic acid according to claim 1.

5. A pharmaceutical composition comprising:

the expression vector according to claim 4 and a pharmaceutically acceptable excipient.

6. A host cell transformed with the nucleic acid according to claim 1.

7. A method for producing a chimeric protein, comprising:

culturing a host cell transformed with the nucleic acid according to claim 1.

8. A nucleic acid encoding a chimeric protein consisting of an amino acid sequence having at least 90% identity to SEQ ID NO: 2.

9. A nucleic acid comprising:

a) a nucleotide sequence encoding a chimeric protein consisting of the nucleic acid sequence of SEQ ID NO: 2; or b) a nucleotide sequence encoding a chimeric protein consisting of an amino acid sequence of SEQ ID NO: 2 in which 1 to 10 amino acids are deleted, substituted, inserted and/or added.

10. A nucleic acid comprising:

a nucleotide sequence encoding a chimeric protein consisting of the amino acid sequence of SEQ ID NO: 2.

11. An expression vector comprising:

the nucleic acid according to claim 10.

12. A pharmaceutical composition comprising:

the expression vector according to claim 11 and a pharmaceutically acceptable excipient.

* * * * *